(12) United States Patent  
Campbell

(10) Patent No.: US 7,446,318 B2  
(45) Date of Patent: Nov. 4, 2008

(54) REMOTE TRIGGERED X-RAY IMAGE CAPTURE DEVICE

(75) Inventor: William E. Campbell, Marietta, GA (US)

(73) Assignee: Merlin Digital Technology LLC, Portland, OR (US)

( * ) Notice: Subject to any disclaimer, the term of this patent is extended or adjusted under 35 U.S.C. 154(b) by 137 days.

(21) Appl. No.: 11/455,141

(22) Filed: Jun. 15, 2006

(65) Prior Publication Data

US 2007/0145280 A1 Jun. 28, 2007

Related U.S. Application Data

(63) Continuation-in-part of application No. 11/317,462, filed on Dec. 22, 2005.

(51) Int. Cl.
*G01T 1/20* (2006.01)
(52) U.S. Cl. ................... 250/368; 378/98.3
(58) Field of Classification Search ........... 378/98.3; 250/368
See application file for complete search history.

(56) References Cited

U.S. PATENT DOCUMENTS

| | | | | |
|---|---|---|---|---|
| 3,483,379 | A * | 12/1969 | Brewster | 378/97 |
| 4,015,126 | A * | 3/1977 | Herrington | 250/214 VT |
| 4,873,708 | A | 10/1989 | Cusano et al. | |
| 5,127,032 | A | 6/1992 | Lam et al. | |
| 5,177,777 | A * | 1/1993 | Niino | 378/98.3 |
| 5,309,496 | A | 5/1994 | Winsor | |
| 5,790,629 | A | 8/1998 | Svensson et al. | |
| 5,844,961 | A | 12/1998 | McEvoy et al. | |
| 5,887,049 | A | 3/1999 | Fossum | |
| 6,178,224 | B1 | 1/2001 | Polichar et al. | |
| 6,194,726 | B1 | 2/2001 | Pi et al. | |
| 6,339,633 | B1 | 1/2002 | Hull et al. | |
| 6,346,707 | B1 | 2/2002 | Vizard et al. | |
| 6,546,076 | B1 * | 4/2003 | Hull et al. | 378/98.3 |
| 2002/0031203 | A1 | 3/2002 | Polichar et al. | |

(Continued)

OTHER PUBLICATIONS

Animal Insides "CR vs. DR . . . The Showdown," <http://www.animalinsides.com/imaging/tutorials/showdown/Showdown_main.htm>, 4 pages (accessed Aug. 10, 2005).

(Continued)

*Primary Examiner*—Constantine Hannaher
(74) *Attorney, Agent, or Firm*—Klarquist Sparkman, LLP

(57) ABSTRACT

Systems and methods are presented herein for generating an X-ray image where the X-ray image generator has no electrical connection with an X-ray source which generates the X-rays. In an exemplary embodiment a photon sensor is positioned behind an x-ray permeable mirror. When the photon sensor senses photons, a camera, positioned outside of the X-ray path, captures a picture containing the X-ray data. A second mirror is positioned such that the path of the X-ray image is folded such that the camera can be positioned outside of the X-ray path, but that the X-ray image still strikes the camera lens. The X-ray data is then sent to a computer for processing. Parameterization is applied to the X-ray data based upon at least one of the species of the animal being taken, the body part depicted in the X-ray, the view depicted and the amount of energy used by an X-ray generator to take the X-ray.

19 Claims, 18 Drawing Sheets

U.S. PATENT DOCUMENTS

2003/0118152 A1    6/2003    Winsor
2004/0005032 A1    1/2004    Nanni et al.

OTHER PUBLICATIONS

Wiley, "The Trauma Workhorse," *Imaging Economics Supplement,* pp. 6-8, Nov. 2004.

Ferdinand, "Bringing Orthopedics Into Focus," *Imaging Economics Supplement,* pp. 14, 15, 18, Nov. 2004.

Smith, "Academic Radiology and *ddR,*" *Imaging Economics Supplement,* pp. 4, 5, 18, Nov. 2004.

Clum, "Is Your Practice Ready for Computed Radiography?," *Dynamic Chiropractic,* vol. 22, issue 2, 4 pages, Jan. 15, 2004.

Varian Medical Systems, "Varian Medical Systems to Supply PaxScan® Flat-Panel X-Ray Image Detectors For Sound Techologies TruDR™ Veterinary Digital Radiography System," <http://www.varian.com.br/comp/050228.html>, 2 pages, Feb. 28, 2005.

Sound Technologies, "The next big thing in digital radiography," <http://www.soundvet.com/Pages/Xray/TruDRequine.html>, 2 pages (accessed May 10, 2006).

Sound Technologies, "TruDR digital radiography," <http://www.soundvet.com/Pages/Xray/TruDR.html>, 4 pages (accessed May 10, 2006).

Freiherr, "Battle of the detectors defines future of DR market," <http://www.diagnosticimaging.com/DR/battle.jhtml>, 8 pages (accessed May 10, 2006).

Universal Ultrasound, "Universal DR & DR Elite," <http://www.universalultrasound.com/productpages/digitalradiography.htm>, 2 pages, 2005-2006 (accessed May 10, 2006).

Manning Innovation Awards News Release, "World's first digital x-ray system achieving global success," <http://www.manningawards.ca/pressroom/2005e.htm>, 5 pages, 2005 (accessed May 10, 2006).

Digital Radiography for veterinarians, "Veterinary digital radiography system benefits," <http://www.iee.com/vetdrs/vetdrsbenefits.html>, 1 page (accessed May 10, 2006).

EPC Search Report dated Mar. 27, 2007, 6 pages, not a publication.

\* cited by examiner

US 7,446,318 B2

REMOTE TRIGGERED X-RAY IMAGE CAPTURE DEVICE

CROSS REFERENCE TO RELATED APPLICATIONS

This is a continuation-in-part of U.S. patent application Ser. No. 11/317,462, filed Dec. 22, 2005, and entitled REMOTE TRIGGERED X-RAY CAPTURE DEVICE.

BACKGROUND

X-ray images can be taken with film in traditional radiography, they can be digitally generated using imaging plates in a process called computed radiography, and digital images can be generated directly from the X-rays themselves in a process called direct digital radiography. Each of these systems has its drawbacks. When film is used to process X-rays, the film must be purchased for each X-ray, and the film must be developed in a process that takes somewhere around 90 seconds to 5 minutes per shot. A patient must wait for the entire developing time to determine if an image is clear or if a retake is needed. Furthermore, processing the films requires that noxious chemicals be used and stored, and disposed.

Computed radiography removes the film from the X-ray process, replacing it instead with a digital imaging plate the same dimensions as the film and placed in the same location. After the imaging plate is exposed to the X-rays, it is placed in an imaging reader, which takes about 90 seconds to generate the digital image. This delay, while not insurmountable when human adults are having their X-rays taken, is much more problematic when the X-ray subject is a small child or an animal which does not understand the need to remain quiet and positioned. Furthermore, the imaging plate is expensive and fragile, an expensive imaging reader must also be used, and generating the digital X-ray image takes roughly the same time as in conventional radiography.

Direct digital radiography uses an imaging sensor in the path of the X-rays to take a direct digital X-ray, which can then immediately be displayed on a computer screen and saved in a digital file for easy reference. However, it is difficult to adequately shield the imaging sensor from the X-rays, requiring that this expensive piece of equipment be regularly replaced. Moreover, there must be an electrical connection between the imaging sensor and the X-ray generator, making retrofitting existing X-ray equipment difficult or impossible.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

In an embodiment, a system is provided which comprises an X-ray to light converter which converts an x-ray image to a light image; a mirror box with a camera opening; a first and second mirror mounted within the mirror box; and a camera mounted substantially outside of the mirror box above the camera opening such that the camera is out the path of the x-rays.

The mirror box is constructed with a first mirror at substantially a 45 degree angle from the camera aperture and a second mirror at substantially an 85 degree angle to the first mirror. This creates a folded light such that an image traveling along the folded light path is reflected by the mirrors, a first segment of the light image crossing a second segment of the light image at least twice, the mirrors substantially focusing the light image on the camera. The mirror box dissipates sufficient heat that no other heat-dissipation device is required for the light.

An ionization chamber can also be included which is mounted substantially outside of the mirror box behind the first mirror. The first mirror allows x-rays to pass through an aperture in the mirror box covered by the mirror, striking the ionization chamber and thereby triggering the camera.

Additional features and advantages will become apparent from the following detailed description of illustrated embodiments, which proceeds with reference to accompanying drawings.

DETAILED DESCRIPTION

The present application relates to technologies for remote-triggered X-ray devices. Described embodiments implement one or more of the described technologies.

Various alternatives to the implementations described herein are possible. For example, embodiments described with reference to flowchart diagrams can be altered by changing the ordering of stages shown in the flowcharts, by repeating or omitting certain stages, etc. As another example, although some implementations are described with reference to specific devices, such as cameras and screens which transform X-rays into light; other devices with the same functionality also can be used.

The various technologies can be used in combination or independently. Different embodiments implement one or more of the described technologies. Some technologies described herein can be used in conjunction with a computer; such a computer could be a desktop computer, a portable computer, a handheld computer, a wearable computing device, a Personal Digital Assistant (PDA), or an intelligent cell phone.

I. Overview

Figure 1A:
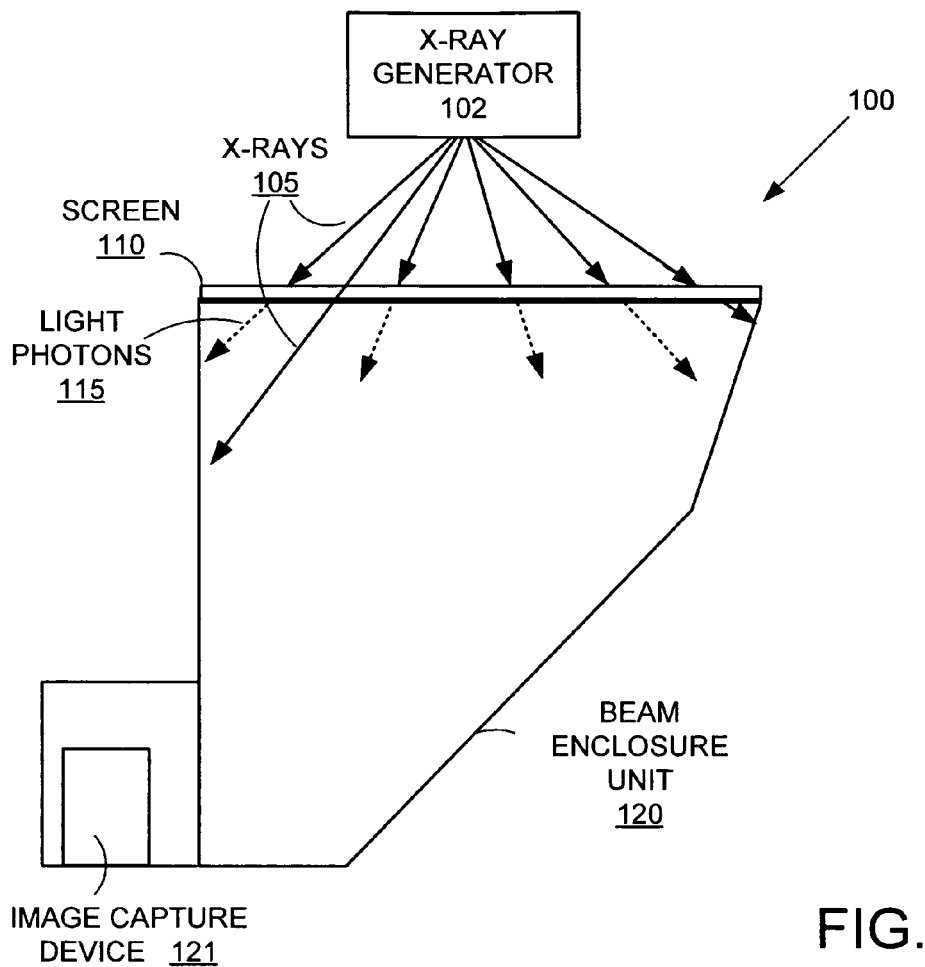
FIG. 1A is an illustration of several aspects of a remote-triggered X-ray capture device including aspects of the enclosure unit in conjunction with which described embodiments may be implemented.
Figure 1B:
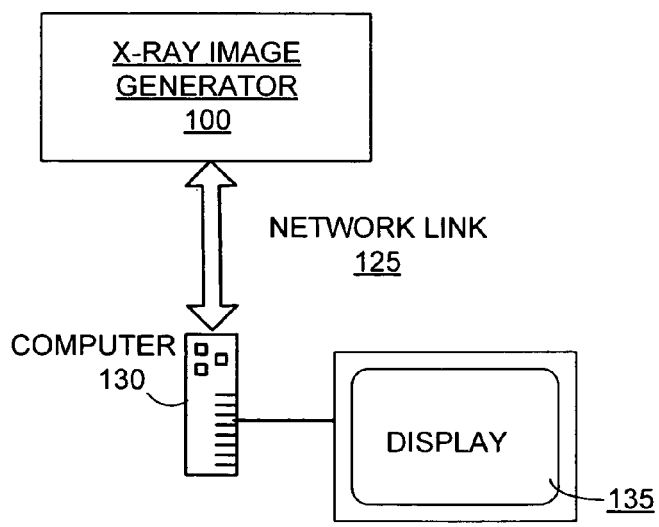
FIG. 1B is an illustration of several aspects of a remote-triggered X-ray capture device which builds on aspects shown in FIG. 1A in conjunction with which described embodiments may be implemented.

With reference to FIGS. 1A and 1B, systems and methods are presented herein for creating a remote-triggered X-ray device 100. The device is designed to be used with existing X-ray generators, as it does not require an electrical connection between the existing X-ray machine and the direct digital radiography recording device. When an X-ray generator 102 is activated, X-rays 105 are directed towards a screen 110. X-rays are electromagnetic radiation with a wavelength between 10 nanometers and 100 picometers. This corresponds to frequencies between 30 PHz and 3 EHz. X-ray wavelengths overlap those of Gamma rays; Gamma rays are generated by transitions within the atomic nucleus, while X-rays are generated by energetic electron processes. For the purposes of these embodiments, all radiation with wavelengths between 10 nanometers and 100 picometers, no matter what the source, should be considered X-rays.

The screen 110 transforms X-rays 105 into light 115, which may be fluorescent light. In some embodiments, the light may be in the visible, the infrared, or the ultraviolet spectrum, or some combination thereof. These screens, sometimes called intensifying screens, generally contain, among other ingredients, a layer of phosphor crystals. When an X-ray photon strikes a phosphor crystal, many light photons are emitted, which will then be photographed to create the X-ray image. Two major types of phosphors used to create intensifying screens for use with envisioned embodiments are calcium tungstate ($CaWO_4$) and various rare earths. Among the rare earths, Gadolinium Oxysulfide and Thallium-doped Cesium Iodide are among the substances suitable for building an intensifying screen. However, other substances that convert X-rays to light, such as metal screens, are also envisioned to be used.

The screen 110, 205 is mounted on the top of the beam enclosure unit 120. This beam enclosure unit 120, in an exemplary embodiment, is installed under a table top. A variety of mounting devices adapted to each type of table manufactured are expected to be used in the installation. When an embodiment is used in a veterinary setting, those mounting in common use in veterinary medicine are used. The beam enclosure unit 120 should be installed such that the system weight is supported and such that an X-ray beam is appropriately aligned during exposure. The support mechanism can allow freedom of motion when an X-ray support tower (not shown) is moved toward either end of the table that the beam enclosure unit 120 is installed underneath. In another embodiment, the beam enclosure unit 120 is installed without a table present.

The aperture of the beam enclosure unit 120 through which the X-rays 105 enter measures, in exemplary embodiments, may be any size, but sizes suitable for a wide variety of X-ray technologies, such as intra-oral X-rays for dentists, as well as X-rays suitable for large animals, extremely large X-rays taken for non-destructive testing are all envisioned. For example and not limitation, aperture ranges from 12 mm×16 mm (or smaller) up to 17"×17" or larger are envisioned. A light-tight cover is also included (not shown) which also may act as support for the screen 110. The screen 110 may be bonded to the light-tight cover. The light-tight cover may be any low molecular weight material such as aluminum, carbon fiber or even cardboard to minimize X-ray absorption. The light-tight cover can be bolted around its perimeter to the beam enclosure 120 with tamper-proof screws.

Figure 2:
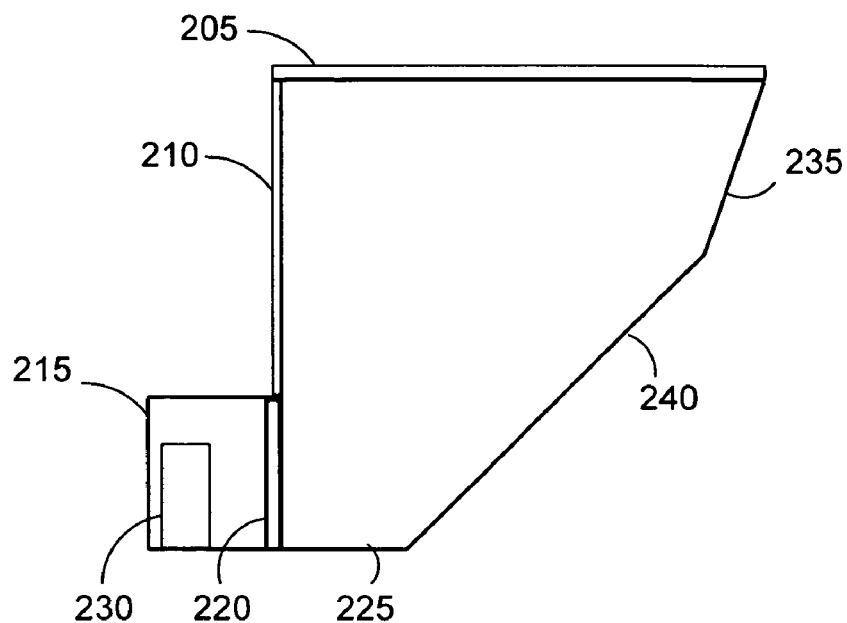
FIG. 2 is an illustration of several aspects of a remote-triggered X-ray image capture device which builds on aspects shown in FIG. 1 in conjunction with which described exemplary embodiments may be implemented.
Figure 3:
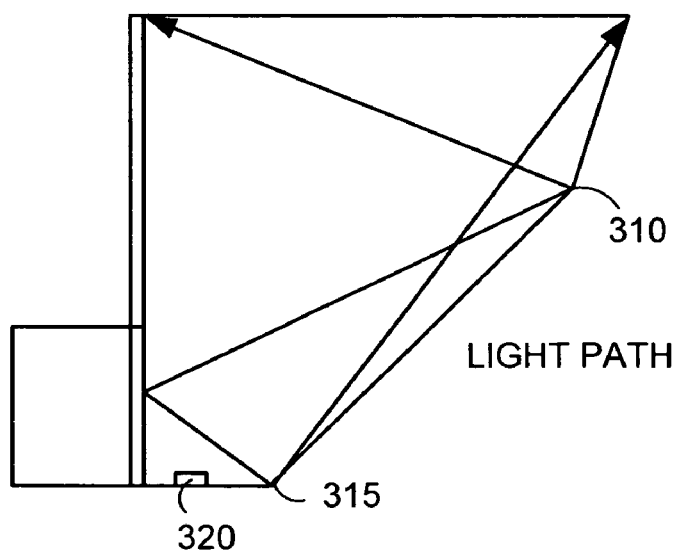
FIG. 3 is an illustration of several aspects of a remote-triggered X-ray image capture device including light paths in conjunction with which described exemplary embodiments may be implemented.

Turning to FIGS. 2 and 3, and with continuing reference to FIG. 1, the light 115 is captured by the accumulator 220, which, in an exemplary embodiment, is designed to minimize quantum efficiency loss and provide an optically flat field. A small amount of adjustment of the light rays entering the accumulator 220 may be provided by the accumulator 220.

A light measuring device such as a camera 230 is placed in an enclosure 215 just behind the accumulator 220. Shielding 210 protects the camera 230 from the X-rays 105. Because of the location of the shielding 210 in relation to the X-rays 105 in the beam enclosure unit 120, steel can be used for the shielding rather than the more common lead, as the camera 230 is out of the direct path of the X-rays. In another exemplary embodiment, lead is used for the shielding. Additional shielding may be placed along other areas where X-rays may penetrate 225, 235. The dangers of X-ray radiation on living tissue is well-known. X-rays are also destructive of sensitive equipment. For example, X-ray exposure can greatly shorten the working life of a camera used to take an X-ray. Shielding the camera 230, as is done here, both by using traditional shielding 210, 225, 235, and by placing the camera 230 out of the direct path of the X-rays, can lead to a much longer camera life, and can greatly reduce the amount of maintenance needed on the X-ray device.

A mirror 240 is also included as part of the beam enclosure 120, in an exemplary embodiment. An accumulator 220 is arranged in front of the camera 230. The mirror 240 reflects the light 115 seen by the camera 230 at an angle that focuses the light 115 across the length of the screen 110. In an exemplary embodiment, the reflected light path is shown at 310, 315. It can be seen that the entire aperture of the beam enclosure unit 120 through which the X-rays 105 enter can effectively be "seen" by the camera 230 through the image reflected in the mirror 240. Thus, when the camera 230 is triggered, the camera 230 captures substantially the entire X-ray image (as translated into light). The mirror 240, in an exemplary embodiment, is mounted at a 45-degree angle, though other angles of mounting are envisioned. Additionally, the mirror 240 may be enhanced by surface preparation to provide additional light reflection when mounted between 43 degrees and 47 degrees to the incident light beam. The mirror 240 may reflect in excess of 97.5% of the available light, and may be aluminum-enhanced, and micro- or pico-ground.

In an exemplary embodiment, there is no connection between the X-ray source 100, shown in FIGS. 1A and 1B and the remote-triggered X-ray device. This allows the X-ray device to be easily retrofitted to existing X-ray sources, as there is no need for an electrical connection between the existing X-ray source and this device. Therefore, wiring diagrams need not be consulted, for example. This allows existing X-ray sources, whose wiring may have been lost, to still be retrofitted with minimum difficulty. In systems whose wiring is known, the expense and time of wiring the two devices together is eliminated. Further, an entire category of timing problems between the systems is also eliminated.

With reference to FIG. 3, a photon detector 320 is provided which triggers substantially at the exact moment that the visible light rays 115 are available to be captured by the camera 230. The location of the photon detector 320 in FIG. 3 is for illustrative purposes only; it can be placed anywhere within the beam enclosure unit 120 that is convenient. It may also be placed outside the beam enclosure unit 120 if by such placement it can still trigger the camera 230 at the time of X-ray generation without being integrated into the circuitry of the host X-ray source. When the camera 230 is triggered by the photon detector 320, it creates a digital image representative of the X-rays. As shown in FIG. 1B, this digital image can then be transferred through a link 125 to a computer 130, which then processes the image and displays it on a computer screen 135. In an exemplary embodiment, the system is used primarily in a veterinary setting.

II. EXEMPLARY SYSTEM EMBODIMENT

Figure 4:
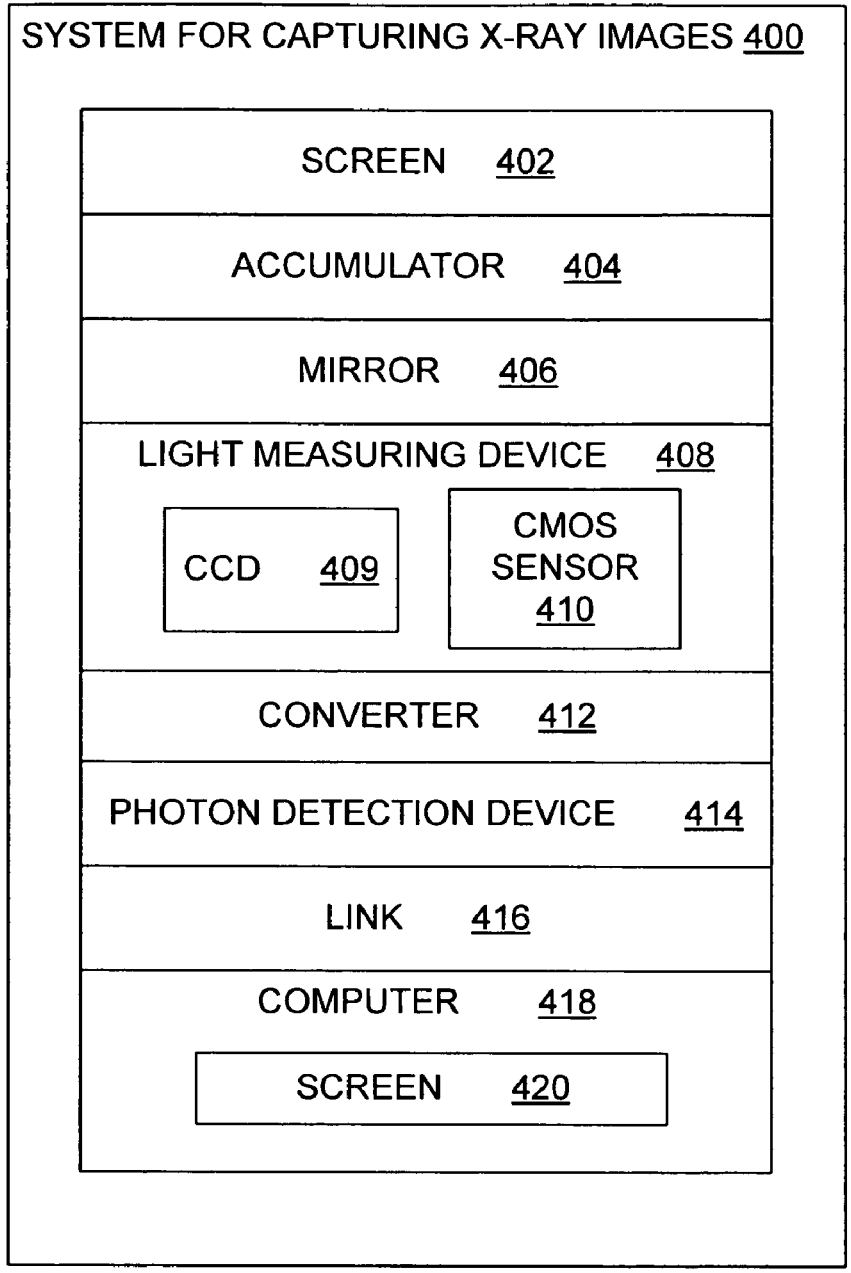
FIG. 4 is a functional block diagram illustrating an embodiment of an example system for capturing X-ray images in conjunction with which described exemplary embodiments may be implemented.

Referring to FIG. 4, a block diagram of a system for capturing X-ray images 400 shows an exemplary embodiment of the systems discussed herein.

The system for capturing X-ray images 400 consists of a screen 402, which converts X-ray photons to light photons. Generally, the screen contains a material, among other components, which, when struck by an X-ray photon, generates light photons. Inorganic salts, also known as phosphors, are among the materials that are suitable to generate light photons when struck by an X-ray photon. If an inorganic salt is used, it will generate florescent light. Only a portion of the X-rays will be absorbed by the screen, causing light photons to be emitted. For example, if calcium tungstate is used, approximately 20 to 40 percent of the X-ray photons will be absorbed; the bulk of the rest will pass through the screen into the beam enclosure unit 120. In comparison, rare earth screens absorb approximately 60 percent of the X-ray photons. Furthermore, the efficiency of calcium tungstate screens at converting X-rays into light is only about one-third to one-fourth that of rare earth screens. However, each materials may be used in exemplary embodiments.

The system also contains a mirror 406. The light rays generated by the screen 402, continue on the same path as that of the initial X-rays that generated the light. The mirror 406 reflects the light rays that strike it at such an angle that the light-measuring device 408 is focused on the screen 402 such that when the light-measuring device 408 is triggered, a view of substantially the entire screen is captured. As shown, the image path from the light measuring device 408 is folded, such that the light rays strike the mirror 406 and are bent such that at least some of the light rays cross paths on their way to the screen. The illustrated embodiment shows the rays bending once; other embodiments can employ image paths that bend the rays multiple times. In an exemplary embodiment, the mirror 406 is placed at a 45 degree angle to the screen 402. In alternate embodiments, the mirror is positioned such that a portion of the screen 402 is captured. Optionally, an accumulator 404 is used to at least partially focus the light on the light-measuring device 408. This light-measuring device 408, in an exemplary embodiment, is a charge-coupled device 409. In an alternate embodiment, a complementary metal oxide semiconductor (CMOS) device 410 is used as the light-measuring device 408. An exemplary embodiment employs more than one light-measuring device.

When the light-measuring device 408 is triggered, each pixel that makes up a light-measuring array in either the charge-coupled device 409 or the CMOS device 410 is struck by some number of light photons, which are then converted to electrons. The number of electrons in each pixel is considered the pixel's charge. A converter 412 then converts the charge into a digital value. Each of the digital values is then associated with a specific gray-scale value, in an exemplary embodiment, to form a detailed black and white image.

In another embodiment, the light-measuring device 408 records the images in color, with each digital value associated with a color, using some color space to assign specific values to the pixels. Examples of exemplary color spaces known to those in the art that could be used in exemplary embodiments are RGB, CNY, CMYK, HSV, HLS, and so on.

In an exemplary embodiment, a large-format charge-coupled device has an 11 megapixel grid, which provides up to 16 bits of grey depth in each pixel, resulting in over 65,000 shades of gray being converted into the eventual image. In another exemplary embodiment, a 4 megapixel grid is used, which provides two line pairs per millimeter resolution on the final image.

As there is no direct electrical connection between the system for capturing X-ray images 400 and the source of the X-rays 422, the system itself must determine when to trigger the light-measuring device 408. It does this using a photon detection device 414, which, when it registers either X-rays or light, sends an activation message to the light-measuring device 408 telling it to "snap the picture." Some embodiments may only trigger the light-measuring device 408 when a number of photons over a background threshold amount are detected. If X-rays are detected, an exemplary embodiment uses an ionization chamber as the photon detection device 414. In some embodiments, a gamma ray detector is used for the photon-detector device.

The digital image in the converter 412, which represents an X-ray of a subject, is transferred to a computer 418 using a link 416. This link may be a network connection. If so, it may be a wireless network connection. Once the computer 418 has the image, it processes it to make it clear and readable on a video monitor such as a computer screen, and then displays it on the video monitor 420.

III. Exemplary Method for Creating X-Ray Images

Figure 5:
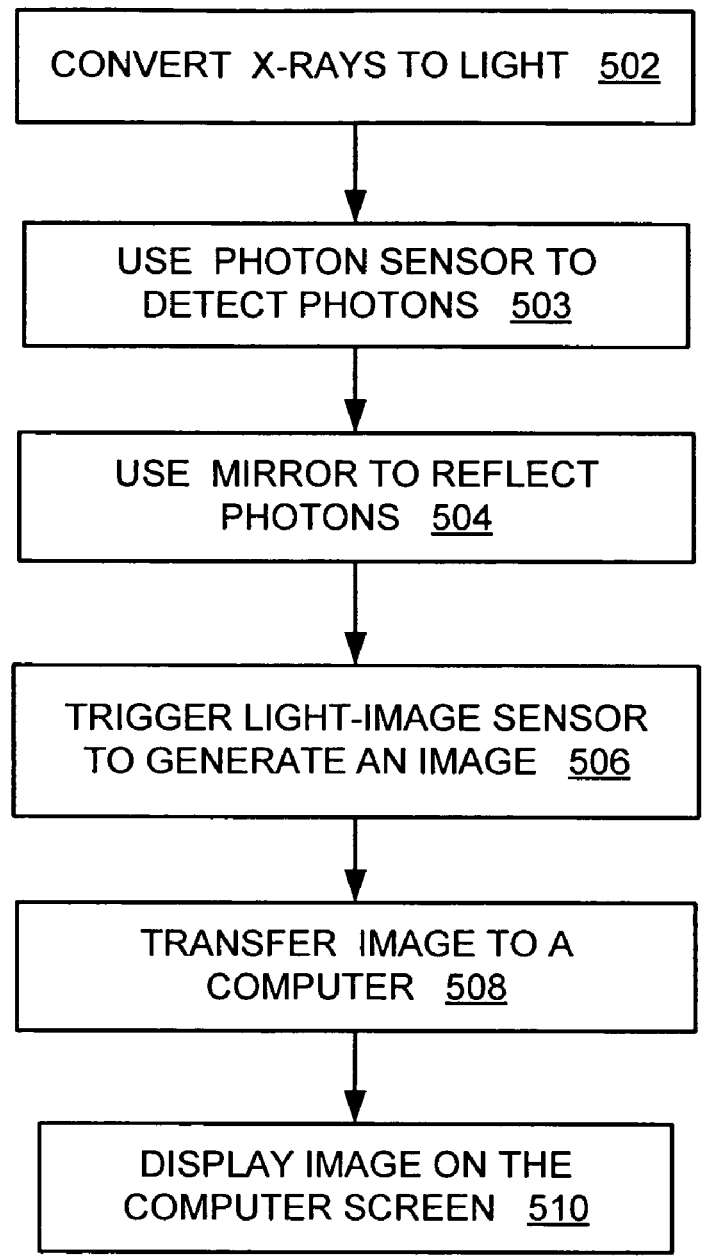
FIG. 5 is an operational flow diagram illustrating a process for capturing X-ray images in conjunction with which described exemplary embodiments may be implemented.

FIG. 5 is an operational flow diagram illustrating a process for creating X-ray images 500. The process begins at process block 502, where X-rays are converted into light. When an X-ray photon hits a phosphor crystal, the phosphor crystal absorbs the X-ray and emits a number of light photons. The size of the phosphor layer and the size of the individual phosphor crystals are some of the factors that determine the level of detail in the eventual X-ray image. The larger the individual crystal and the thicker the phosphor layer, the more spread-out the individual light photons are that are generated by the crystal. The image detail is degraded by the size of the light spread, as the same amount of information is smeared over a larger area. These considerations can be taken into account when determining the optimal material for a given screen.

The process continues at process block 503, where a photon sensor is used to detect whether X-rays or light rays are present. At process block 504, a mirror is used to reflect the light used by a light-measuring device such that essentially all of the light converted by X-rays can be "seen" by the light-measuring device, even if the light-measuring device is out of the direct path of the X-rays.

The process 500 is independent from an X-ray source process which creates the X-rays, so a method internal to process 500 must be used to determine when an X-ray machine has taken an X-ray. When X-rays or light rays are detected at process block 506, a light-image sensor is triggered, which generates an image corresponding to the X-ray. As has previously been detailed, this light image sensor may be a charge-coupled device, a CMOS device, or another device suitable for translating light energy into digital output.

At process block 508, the image is transferred to a computer. The transfer may take place through a network connection. The network may be a local or wide-area network. Furthermore, the network may be wired or the image may travel using a wireless network. In exemplary embodiments, the image is sent through a wireless connection to a communication device, such as a laptop or a portable communication device such as a PDA or an internet-enabled cell phone.

At process block 510, the image, after it has been processed by the computer, is displayed on a computer screen. The processing comprises turning the digital representation into an image that can be viewed on a screen, and may comprise certain modifications to the image, as are known to those of skill in the art. For example, if the image was initially exposed for too long and is too dark, an algorithm may be employed which "lightens" the image, making it easier to read. In some embodiments, an algorithm may be employed on some images to sharpen specific areas, increasing contrast over what would otherwise be seen. A variety of other visualization techniques may be used as well, such as thick-slab rendering, shaded volume rendering, shaded surface display, multi-planar reformatting, flexible clipping, maximum intensity projection, perspective viewing, and the like.

Processing may be provided which allows the image to be transferred to a different system, or which stores the image in a standard format, such as DICOM, CMP, PNG, JPEG, TIFF, GIF, or other widely-available format. Some embodiments may include algorithms which store the images in a proprietary format, the proprietary format being a format used by a single vendor or a limited number of vendors. Other processing, as known to those of skill in the art, is also envisioned.

IV. Exemplary Method to Display an X-Ray Image

Figure 6:
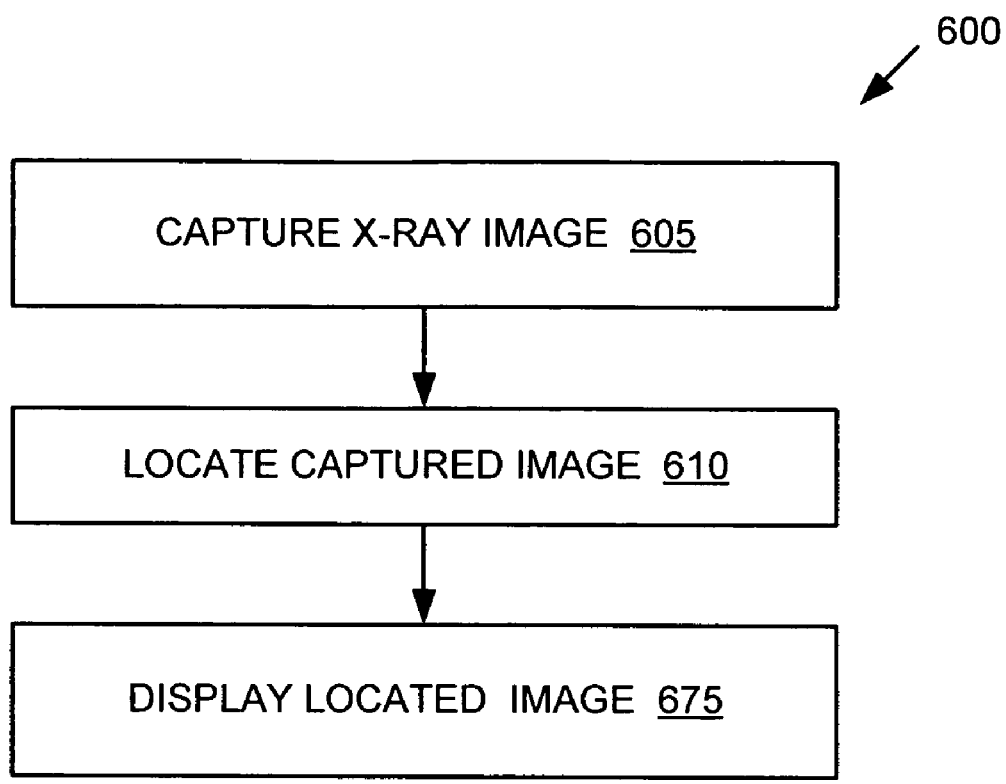
FIG. 6 is an operational flow diagram illustrating a process for displaying an X-ray image.

FIG. 6 shows an exemplary method 600 to display an X-ray image. The X-ray image to be displayed may be of an adult human or child, or of an animal, such as would be seen in a veterinary practice. The animal may be very large, such as a horse, or much smaller, such as a ferret. At 605 the X-ray image is captured. The capture may be performed by a system such as that shown at 400 in FIG. 4. In some embodiments, a screen such as that shown at 110 in FIG. 1 may be used to transform the x-rays into light rays prior to the x-ray image being captured, using a method that is sometimes called indirect conversion. In other embodiments, no such screen is used—that is, the x-rays are directly converted into the x-ray image, which may be a digital image. At 610, the captured image is located. The exemplary method 600 may be performed by a system, such as that shown at 400 wherein the X-ray source 422 is unattached to the system for capturing x-ray images 400. In such a case, the X-ray data must be cropped out of larger image with unexposed edges. At 675, the located X-ray data is displayed.

V. Exemplary Schematic Diagrams of Exemplary X-Ray Images

Figure 7A:
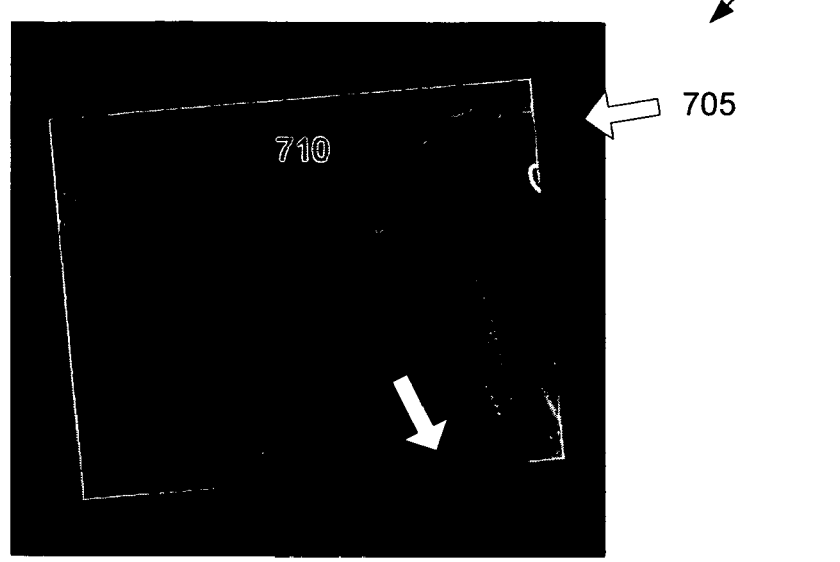
FIGS. 7A-C are exemplary schematic diagrams showing the position of X-ray data within a captured X-ray image.
Figure 7B:
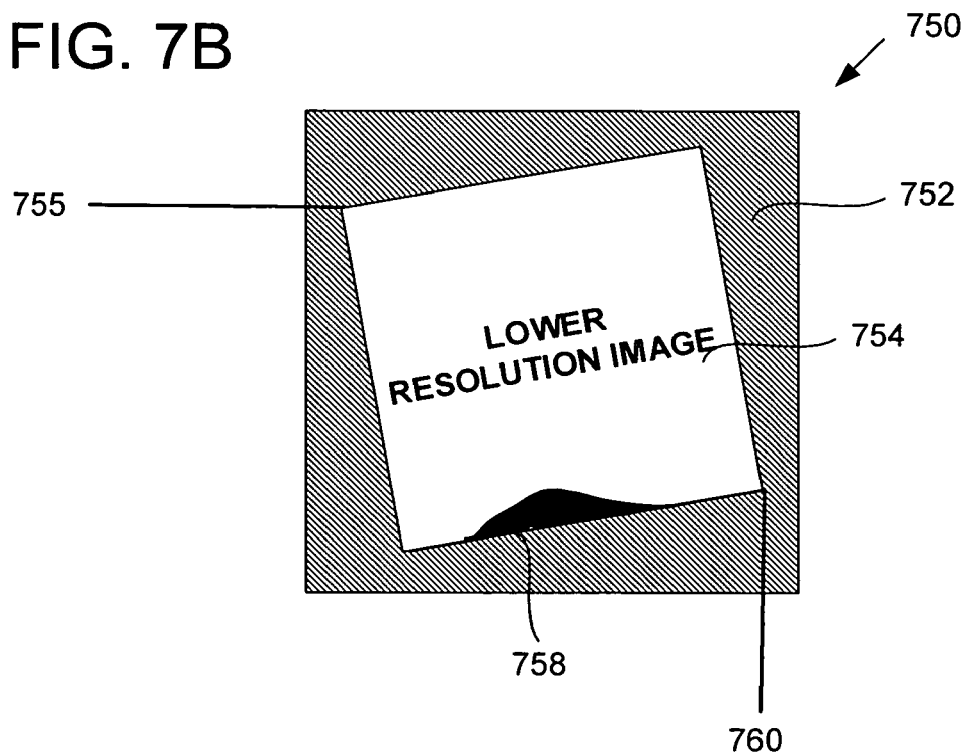
Figure 7C:
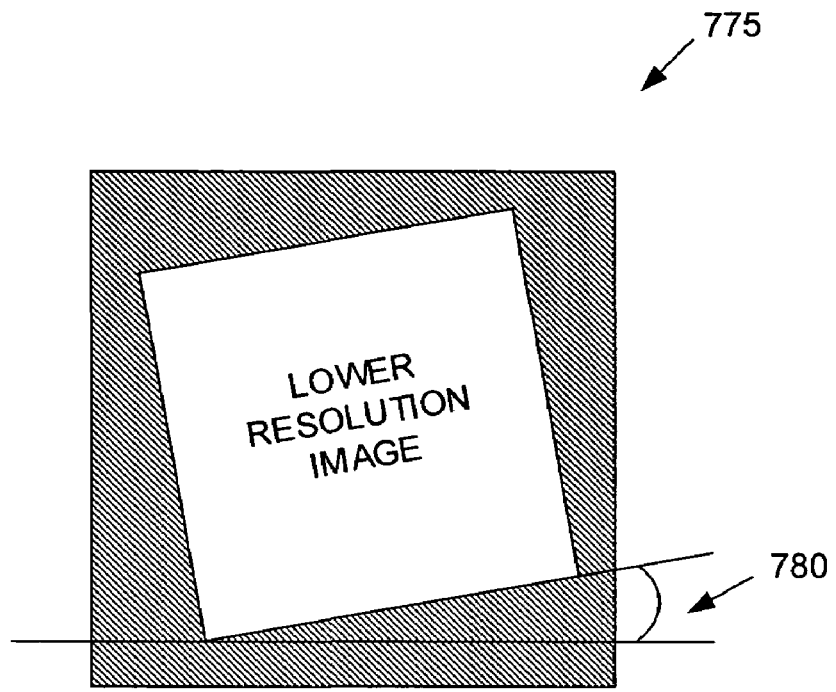

FIGS. 7A-C are exemplary schematic diagrams showing the position of X-ray data within a captured X-ray image. A captured X-ray image 700 is shown in FIG. 7A. The image is composed of the actual X-ray image data 710 and junk data values 705 which represent unexposed portions of the image. FIG. 7B shows a reduced-resolution x-ray image 752. Also shown are corners 755 and 760, which can be located to determine the exact location of the X-ray image data 710. FIG. 7C shows the angulation 780 of a captured X-ray image 775.

VI. Exemplary System to Display an X-Ray Image

Figure 8:
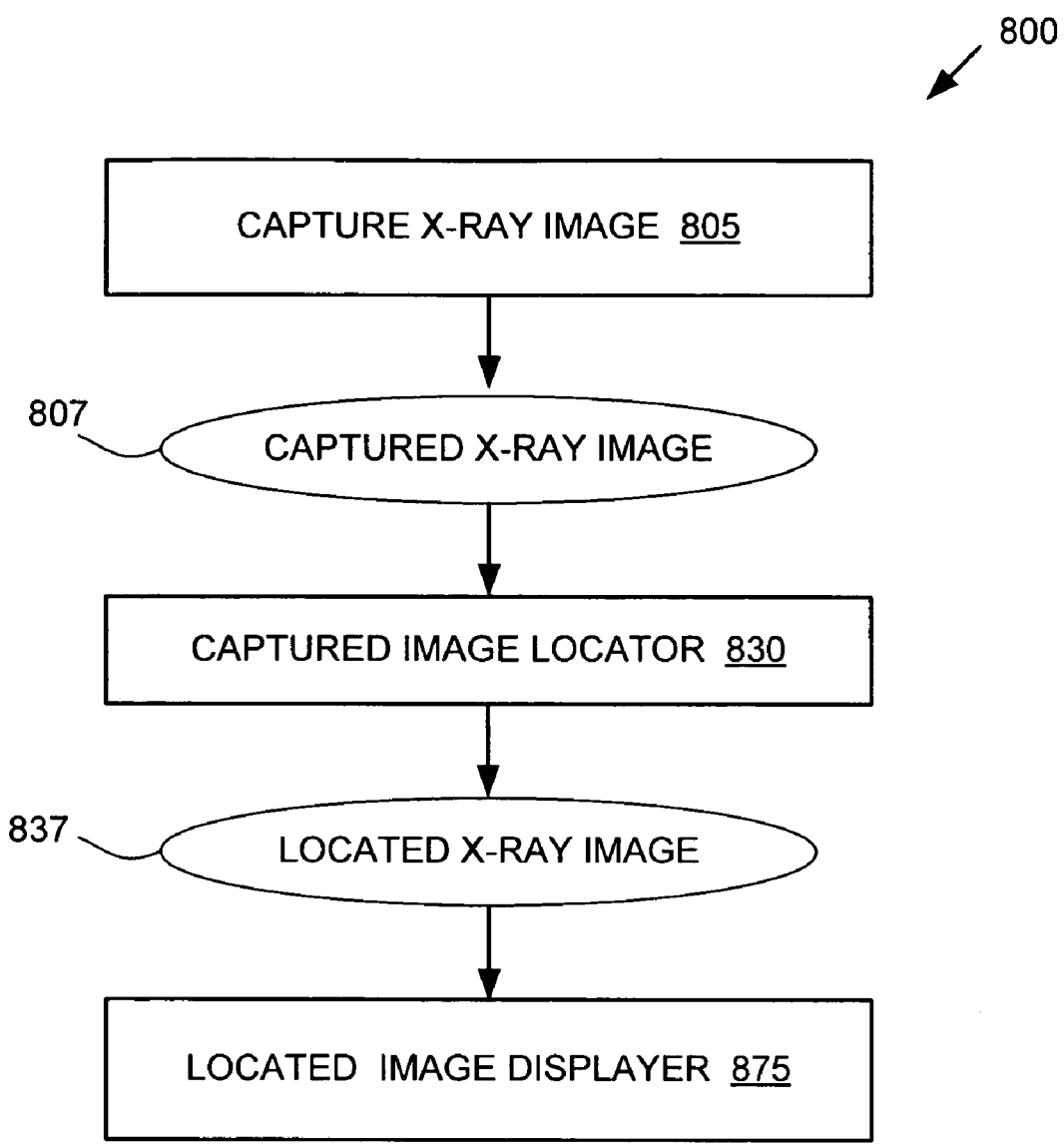
FIG. 8 is a block diagram showing an exemplary system for displaying an X-ray image.

FIG. 8 is a block diagram 800 showing an exemplary system for displaying an X-ray image. At 805, an X-ray image is captured. This image may be captured using a system, such as the system 400 wherein the X-ray source 422 has no electrical connection with the X-ray image capturer 400. The capturing itself may be done by a charge-coupled device or a CMOS sensor, or a different sort of light- or x-ray sensitive device. For example, an exemplary embodiment may use an electronic array made at partially from, for example, amorphous selenium, which converts x-rays directly to an electric charge. Another exemplary embodiment uses an electronic array made at least partially of amorphous silicon. The image may be captured as a digital representation, and may be represented as a grayscale digital image. In at least some embodiments, the image is captured as a combination of colors other than black and white. In a grayscale digital image, the image is captured as a grid of pixels, each pixel having a value representing a shade of gray. Possible digital representations for the original capture comprise 8 bit, 12 bit, 16 bit, or a different resolution.

In an 8 bit grayscale image, the image is generally captured as 256 shades of gray. In a 12 bit grayscale image, there are 4096 shades of gray, with, in some conventions, 0 being black, and 4095 representing white. In a 16 bit grayscale image, there are 65,536 distinct shades of gray. A monochromatic image may contain only black and white, and may be considered a 1-bit grayscale or a binary image.

The captured image is shown at 807. The actual x-ray image data may not take up the entire captured X-ray image, that is, there may be dark areas without data along the edges of the picture, as shown at 705 in FIG. 7A. At 830, the captured image 807 is located within the larger image generated when the X-ray image is captured. This creates a located image 837. At 875, a displayer displays the located image 837. The image may be displayed, for example, on a display 135 as shown in FIG. 1B. Even though the exact size and angulation of the X-ray data may not be known, the data itself is expected to be rectangular. Therefore, some embodiments include squaring off the edges that have been located; that is finding data points along at least two edges and the connecting the points in such a way that a rectangular image is determined.

In some embodiments, the displayer displays an image prior to the image being located 837. This can be done to show that a captured image has been received, to facilitate placement of the subject on the X-ray, and the like.

VII. Exemplary Method to Locate a Captured Image

Figure 9:
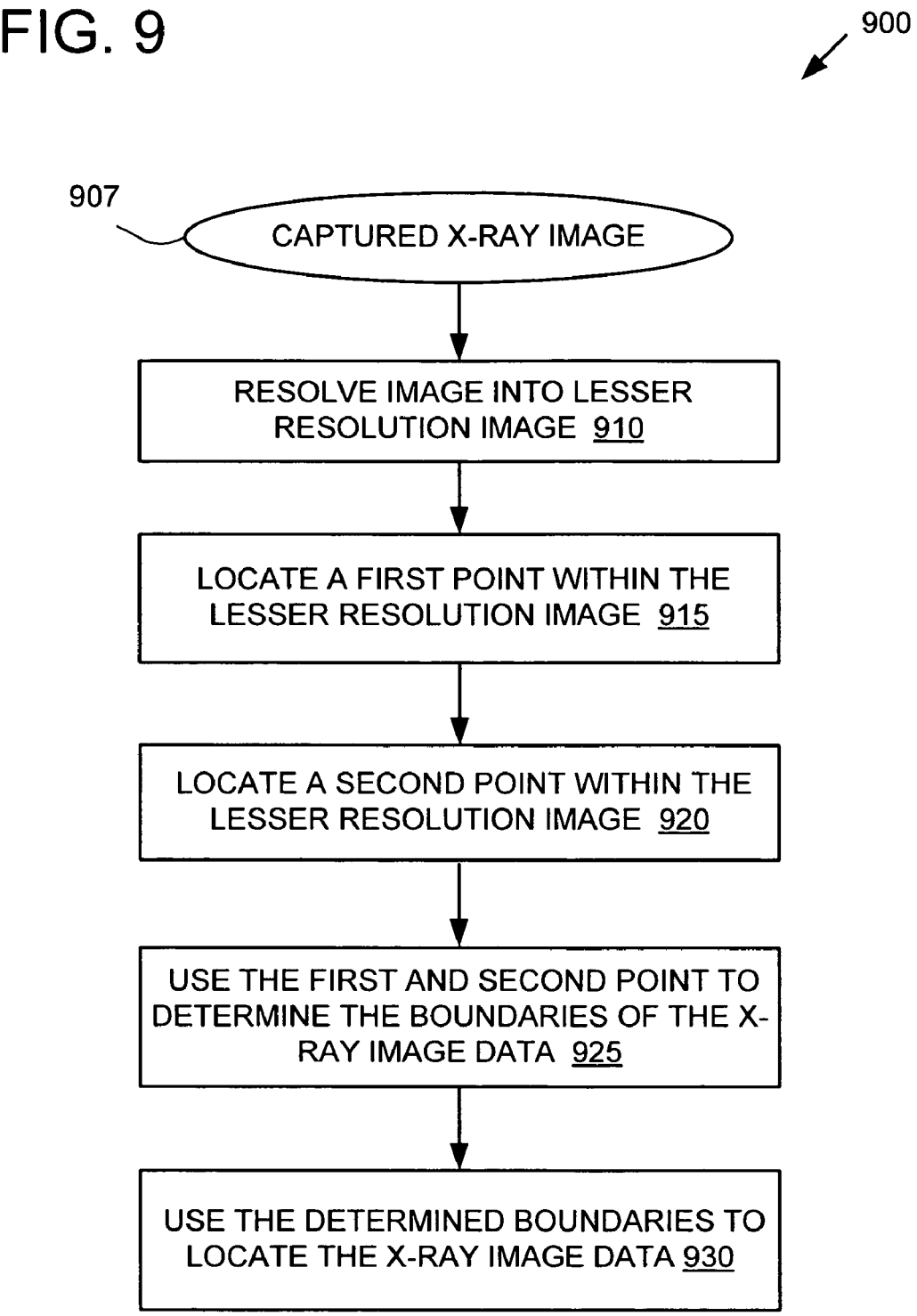
FIG. 9 is an operational flow diagram illustrating a process for locating an x-ray image within a larger captured image.

FIG. 9 at 900 shows an exemplary method for locating an x-ray image within a larger captured image. The method 900 can be performed, for example, by the captured image locator 830 shown in FIG. 8. It is important that only the image itself be captured, as the processing done to the x-ray image is such that junk data values (values incorporated into the image that should have been cropped) can throw off processing that is done to filter and otherwise enhance the image. At 907, a captured X-ray image is received. At 910, the captured image is resolved into an image with lesser resolution.

For example, the original captured image could be a 12-bit grayscale image, with 4096 possible values at each pixel location. These values could be reduced to a 1-bit monochromatic image, that is, two values only (typically but not necessarily black and white) using a variety of methods known to those of ordinary skill in the art. At 915, a first point in the image is located. When an X-ray image does not take up the entire digital representation, such as may happen when the X-ray generator is misaligned with a beam enclosure unit 120 (FIG. 1) the areas that weren't exposed will be black, or close to it, as opposed to the X-ray itself, which will have a much broader range of grayscale values. Resolving the original gray-scale representation to a lower resolution image has the purpose of making the differences between the data and the unexposed edges clearer.

In some instances, the grayscales from black to the middle value may be resolved to black, with the rest of the grayscale images resolved to white. For example, in a 12-bit grayscale image with 4096 total grayscales, the values 0 to 2047 could be mapped to 0, while the values 2048 to 4095 could be mapped to white. In other instances, different mappings may be chosen, such that, for example, the lighter colors are favored. In such an instance, more values could be mapped to white—for example and not limitation, the values 1500-4095 could be mapped to white, with the rest mapped to black. In yet other embodiments, the lower values are mapped to white, while the higher values are mapped to black, etc. This should give the result that the unexposed film is resolved to black (or the shade chosen) and the x-ray data itself is resolved, essentially, to white (or the shade chosen).

Generally, the actual anatomy that appears on the x-ray after the resolving 910 will be white (or the chosen color), but there may be valid areas around the actual x-ray image which are black, but which were exposed and as such are a part of the x-ray. For example, in the x-ray image 710 (FIG. 7A) the area below the animal belly marked with the arrow is black, even though this is a legitimate portion of the x-ray image, as opposed to the unexposed edges 705. For example, the area 758 (FIG. 7B) represents a similar area to that marked with the white arrow (FIG. 7A) prior to the resolving step 910, that is, an area which, although part of the x-ray data, appears the same as the unexposed film as there is no corresponding animal structure at that location. After the resolving step 910, it has resolved to black, even though it is within the located x-ray image 837 (FIG. 8).

In an exemplary embodiment, more values than just black and white are chosen for the lower resolution image, for example, the image may be resolved to a two-bit grayscale image with four values.

At 915, a point within the x-ray data itself is located. The points outside the X-ray data itself 752 (FIG. 7B) are themselves black, in the illustrated embodiment. The data 754 (FIG. 7B) itself in this embodiment is expected to be white. So, locating a point within the x-ray data is equivalent to finding the first white point 755 along an axis of the captured x-ray image 750. In some embodiments, as the exact location of the image is not known, some point along axis may be first located, and then, using that point, the "corner" 755 is located. A tracking algorithm may be used to locate a specific point, and/or the corner, or another method may be used.

Once a first point is located, then a second data point 760 is located, as shown at process step 920. This point may be discovered by reversing the process used to find the first point. That is, if a point was discovered by looking along the x and y axes, this point could be discovered along the -x and -y axes. In some embodiments, another "corner" is located. That is, the point itself is white (in the exemplary embodiment) and the next points along both the x and y axes are black.

Once the two points are located, then the boundaries of the x-ray image data are determined 925.

Due to the vagaries of x-ray data, the point located may not be at the edge of the data, rather, it may be located in an area such as the area 758 which appears to be unexposed, but actually is just a legitimate dark portion of the picture. Several methods may be used to protect against such an image being mistakenly truncated. For example, two perpendicular edges of the data may be plotted, with the edges then extended to produce a reasonable representation of a corner. The entire edge, in some embodiments, is not plotted, rather enough data points are discovered to extrapolate an edge. Once an edge is extrapolated or determined, the angulation of the x-ray data can be determined. The x-ray picture may not be correctly aligned with the camera, such that the picture is at an angle, as can be seen at 775 in FIG. 7C. In some embodiments, angle 780 that the x-ray data is off true is used to determine the boundaries of the x-ray data 925.

Figure 10:
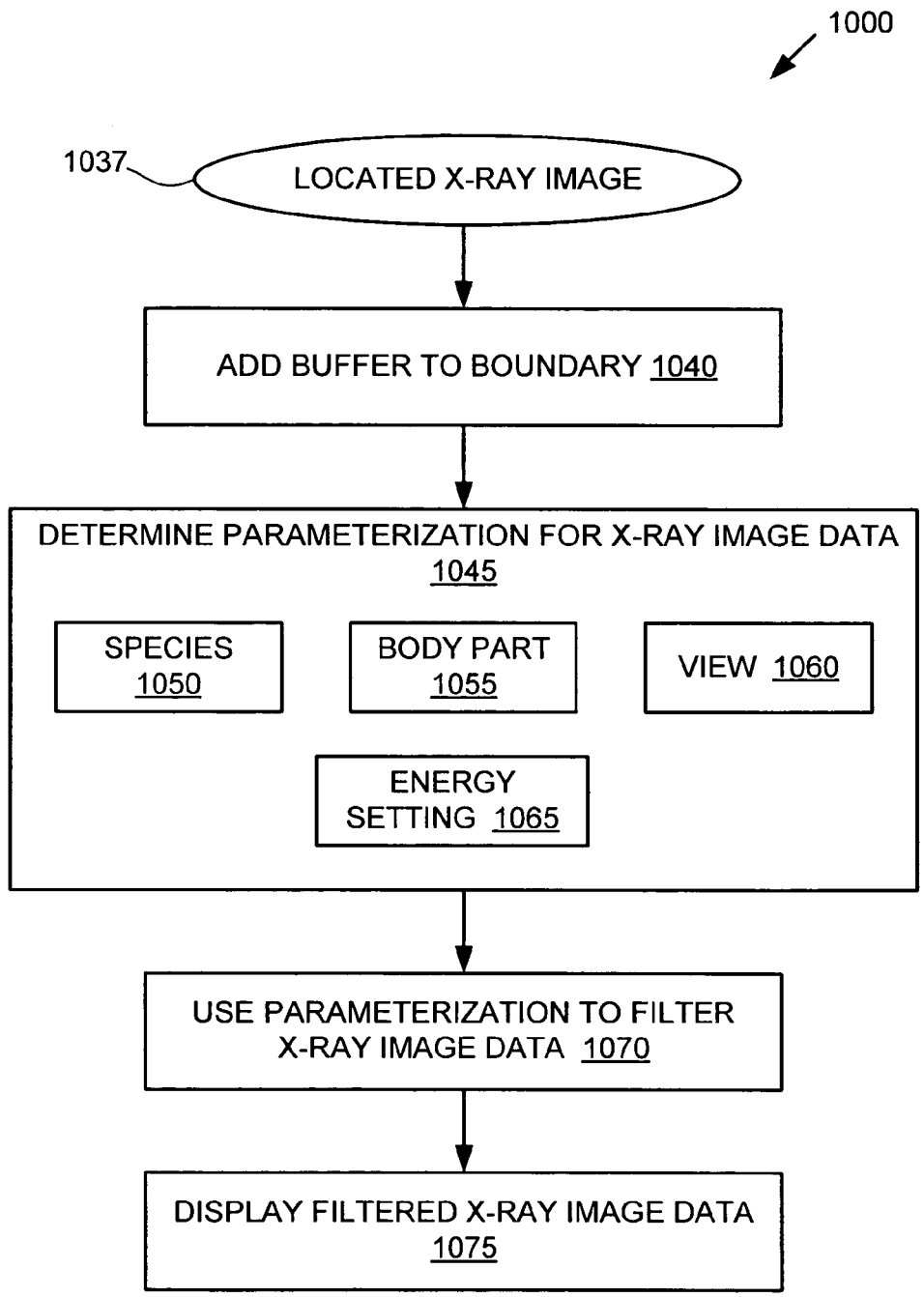
FIG. 10 is an operational flow diagram which is a continuation of the process for locating an x-ray image within a larger captured image illustrated in FIG. 9.

At 930, the determined boundaries are used to locate the boundaries of the actual x-ray image 710 producing a located x-ray image 1037 (FIG. 10).

Method 1000 at FIG. 10 is a continuation of the method shown in FIG. 9. The located x-ray image 1037, in some embodiments, has a buffer applied around the border 1040. This buffer may be a percentage of the total image, such as $1/1000^{th}$ of the image, or a set number of pixels, such as 30. In another exemplary embodiment, the size of the buffer depends on the angulation of the image, so that pictures with a higher angulation are given a bigger buffer.

Figure 12A:
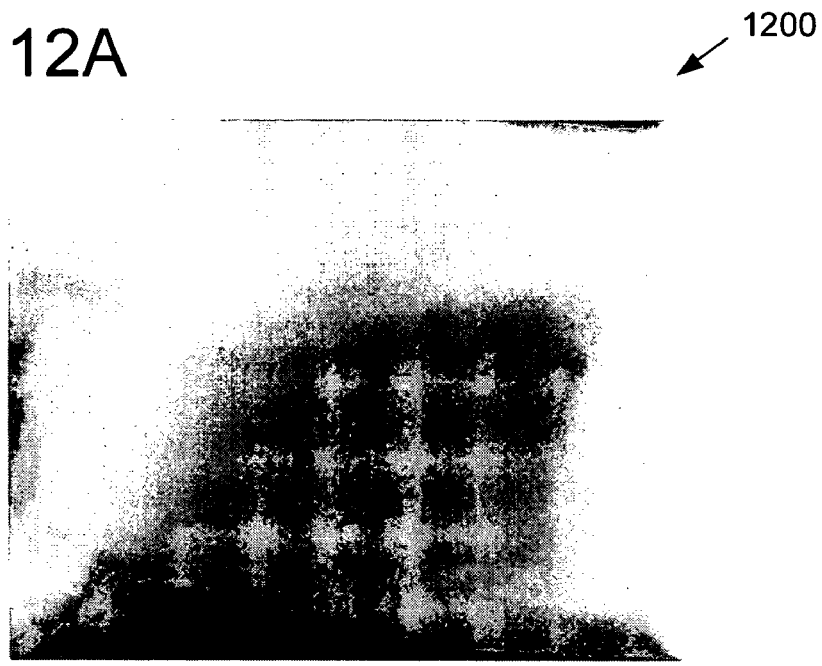
FIGS. 12A and B are X-ray images before and after applying parameterization.
Figure 12B:
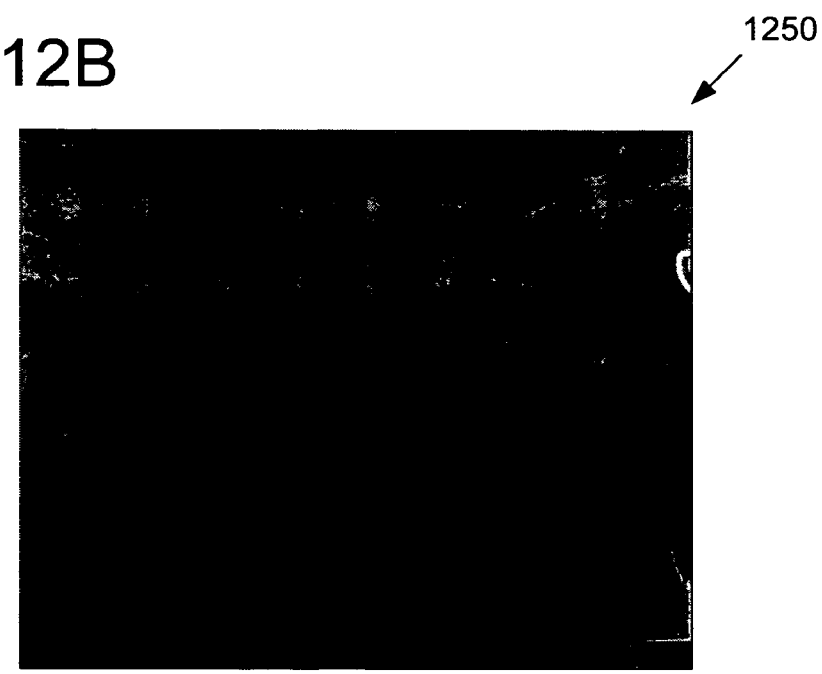

At 1045, parameterization is determined for the x-ray image. Images are often displayed using only a subset of the possible grayscales that make up the original image. For example, often 256 shades are chosen; a number that correlates with the number of colors a human can easily distinguish and with the resolution of certain computer monitors. A parameterization determines how to apply digital high frequency, low frequency, and band pass algorithms to the original shades in a predetermined amount to produce a picture with greater clarity than the original x-ray image. For example, FIG. 12A at 1200 shows an x-ray image of a dog's torso prior to parameterization, and FIG. 12B shows the same x-ray image after it has been filtered using an appropriate parameterization. The image is much clearer, with specific bones and portions of the soft tissue now visible.

Due to the large differences in bone density, bone placement, bone thickness, location, tissue structure, etc., between different types of animals and even between different breeds of the same species (Chihuahua x-rays may require different parameterization than Great Dane x-rays), better results are produced by having parameterization based on a variety of factors. For example, the parameterization can be based, at least in part, on one or more of the following factors: the species of the animal whose x-ray is being taken 1050, the specific body part 1055, the view 1060, the thickness of the bone being x-rayed, and the energy setting 1065 that is being used.

At 1070, the parameterization chosen is used to filter the located, buffered, x-ray image. In some embodiments a separate filter is applied prior to the parameterization 1070. At 1075, the filtered image is displayed. The display may be on a local computer screen, such as the display 135 in FIG. 1B or may be displayed at a remote location after having been transferred through a network link.

VIII. Exemplary System for Generating X-Ray Image Data

Figure 11:
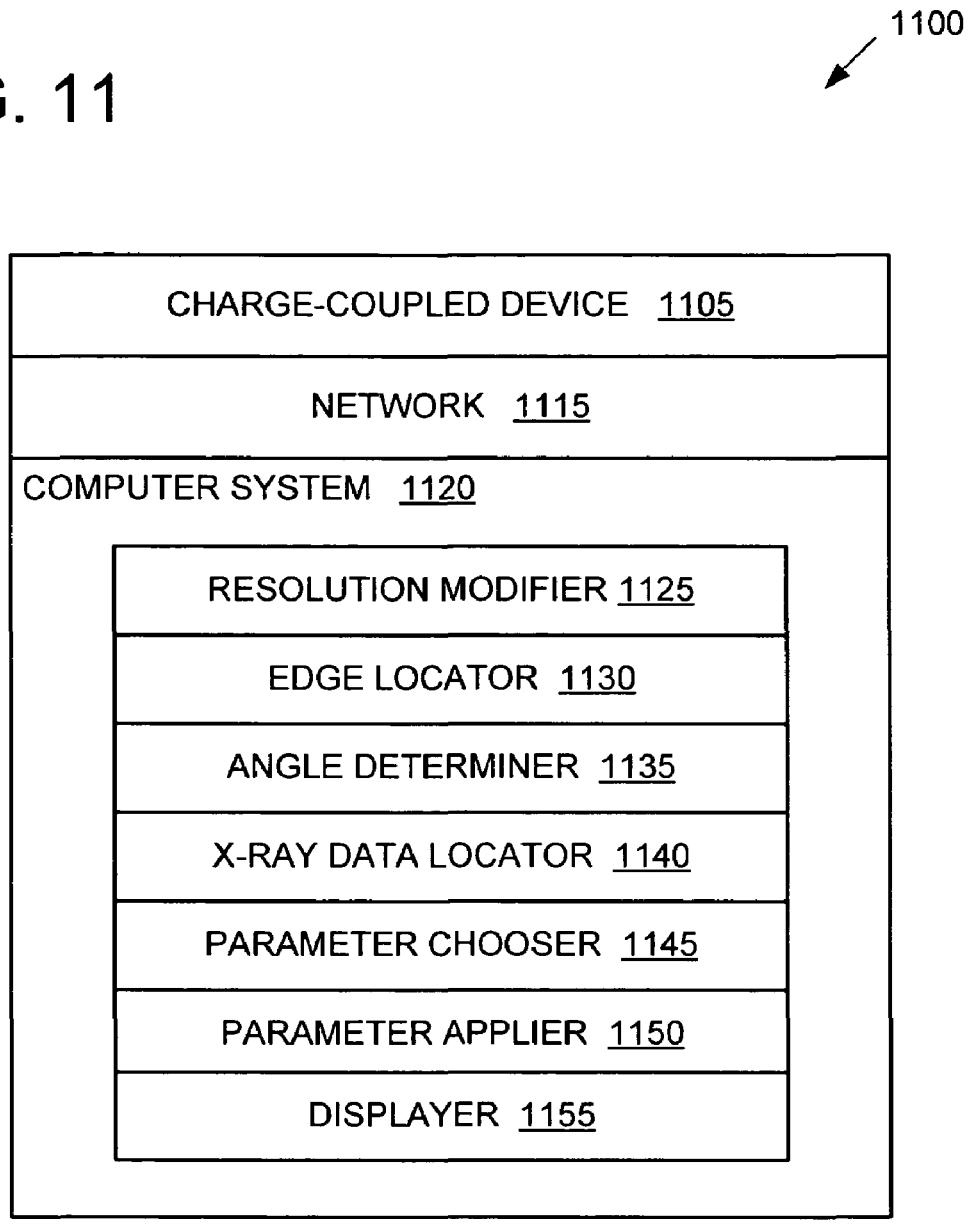
FIG. 11 is a block diagram illustrating an exemplary system for displaying x-ray image data.

FIG. 11 shows an exemplary system for displaying x-ray image data, such as the data generated at 506 in FIG. 5. The system comprises a charge-coupled device 1105 for taking a digital picture of an x-ray, the x-ray rays having been transformed into light rays, as is shown in FIG. 1A and the associated text. The system further comprises a network 1115, which is operable to transfer the picture from the charge-coupled device to a computer system 1120, which may be a remote computer system. The network 1115, which may be wireless, allows the x-ray to be transferred to the computer system 1120. The network 115 may also comprise a simple cable transfer from the charge coupled device 1105 to the computer system 1120.

The computer system 1120 comprises a resolution modifier, which can change the resolution of the picture from, for example, a 16 bit grayscale image to a 1 bit grayscale image. The computer system 1120 also comprises an edge locator 1130 and an angle determiner 1135 which are operationally able to crop the actual x-ray data from the larger picture such that junk data values along the edge representing non-exposed portions of the x-ray are removed. Examples of such junk data values are shown at 705 of FIG. 7A. An X-ray data locator 1140 can then use one or more of the edge locator 1130 and the angle determiner 1135 to locate the x-ray data image within the picture taken by the charge coupled device 1105. A parameter chooser 1145 is operationally able to determine parameters that will be used to filter the x-ray data image. The specific parameters chosen for a specific image may be based, for example, on such values as the species of the animal being x-rayed, the body part being x-rayed, the specific view of the x-ray, and the energy setting used for the x-ray. Once the parameter is chosen, a parameter applier 1150 can be used to apply the parameter to the x-ray to produce a parameterized x-ray. A displayer 1155 is also included which allows the parameterized, filtered, x-ray to be displayed. The x-ray may also be displayed at intermediate stages, such as prior to cropping, and prior to filtering. The displayer may be directly connected to the computer system 1120, or may be connected through a network link, allowing the x-ray to be displayed remotely.

IX. X-RAY DEVICE ENCLOSURE UNIT EMBODIMENTS

Figure 13A:
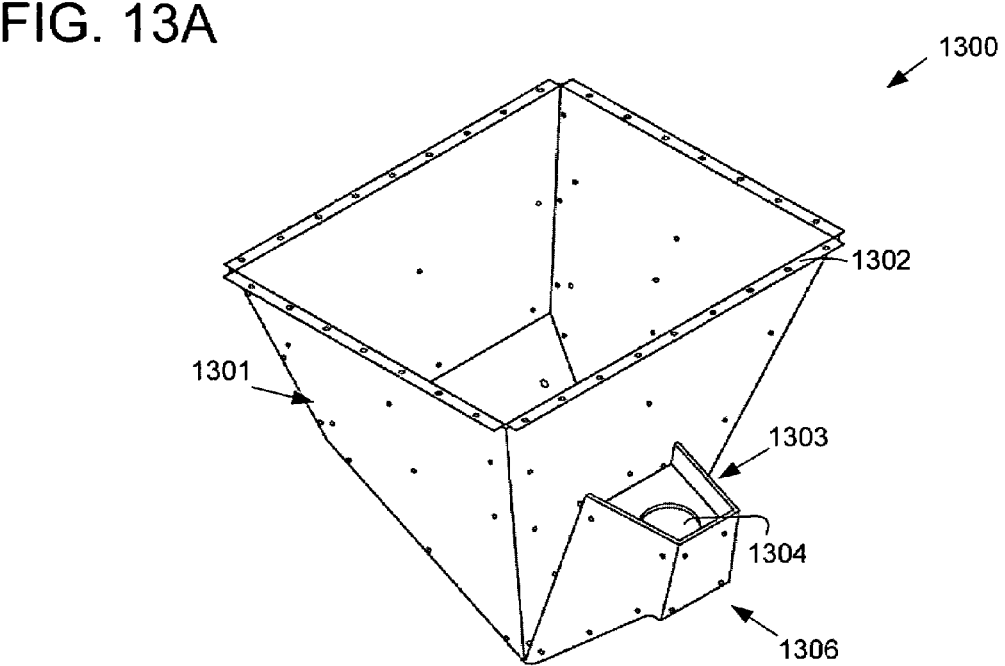
FIG. 13A is a perspective view of an embodiment of the x-ray device enclosure unit.

FIG. 13A is a perspective view of an embodiment of the x-ray device enclosure unit 1300, which may be a mirror box 1301. A light measuring device (such as the light-measuring device 408 of FIG. 4) such as a camera is mounted at 1303, preferably outside of the x-ray device enclosure itself and having a camera opening 1304. The camera opening 1304 may optionally be covered by a light-permeable membrane. This opening is also shown at 1404 (FIG. 14) and at 1504 (FIG. 15). The top of the enclosure unit may be surrounded by a flange 1302, which, in some embodiments, is filled at the corners and welded to create a continuous flange. The mirror box 1301 (such as the beam enclosure unit 120 at FIG. 1) dissipates sufficient camera heat such that that no other heat-dissipation device is necessary for the operation of the camera.

Figure 13B:
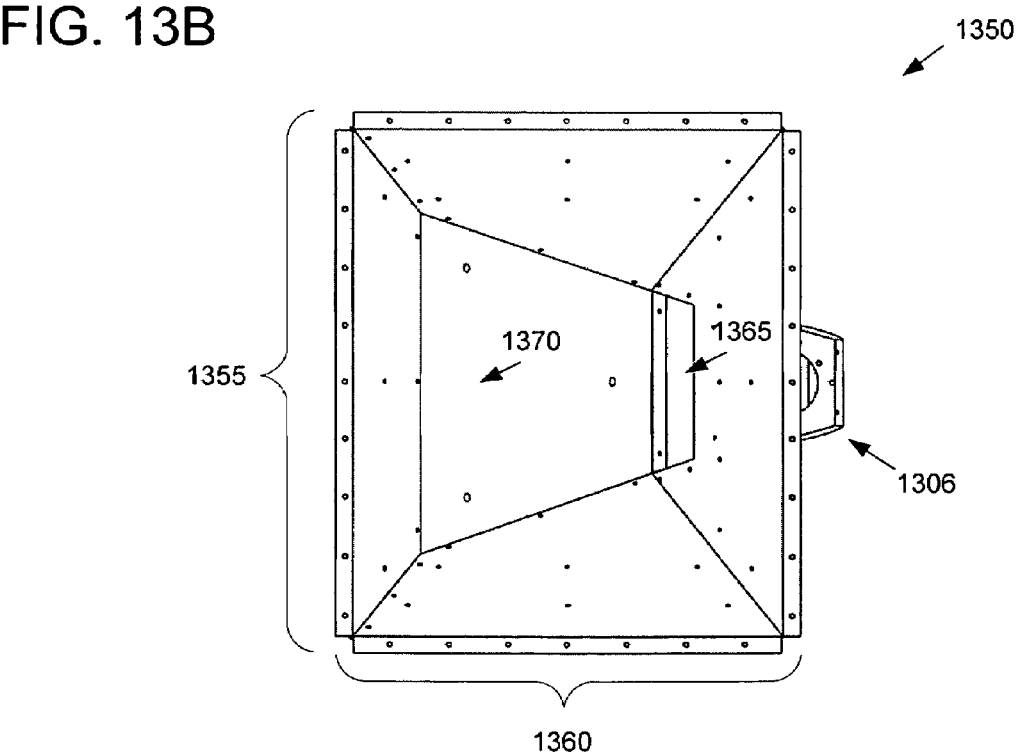
FIG. 13B is a plan view of the embodiment of the x-ray device shown in FIG. 13A.

FIG. 13B is a plan view of the embodiment of the x-ray device shown in FIG. 13A. A camera box 1306 is shown, which is attached to the sides of the mirror box but is otherwise open, so that a camera mounted on camera mount 1303 can be exposed to an x-ray image. A perspective view of the opening between the camera box 1306 and the mirror box 1301 is shown at 1365, this view can also be called the aperture. Other views of the camera opening (or aperture) are shown in FIG. 15 at 1565 and in FIG. 16B at 1665. A mirror, such as the mirror 406, can cover all or a portion of the surface shown at 1422. In an exemplary embodiment, this mirror is at a substantially 45 degree angle to the camera opening 1365. In an exemplary embodiment, the dimensions of the mirror box opening 1360 is 15.62 inches, with the dimensions at 1355 being 18.62 inches.

Figure 14:
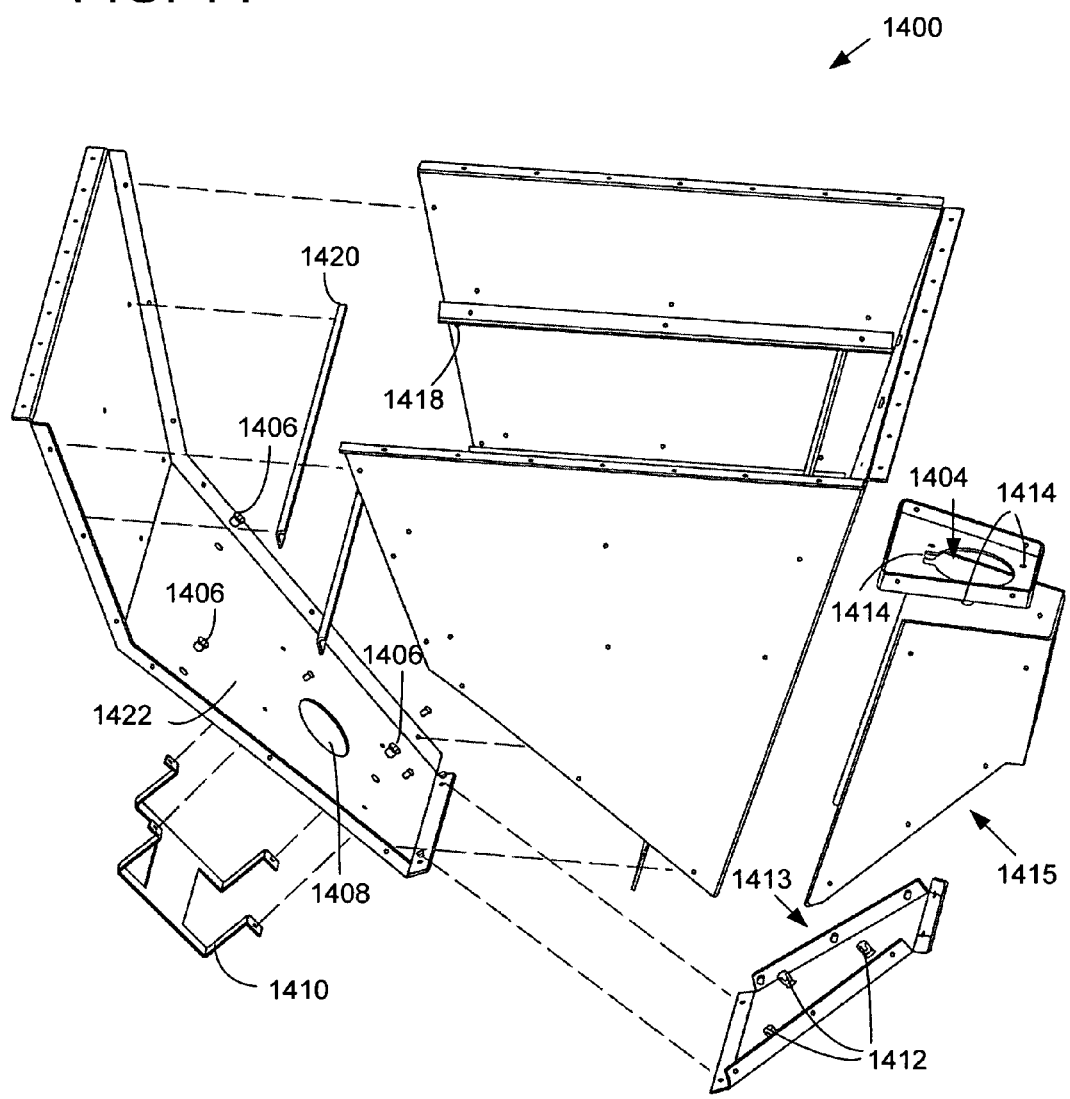
FIG. 14 is an exploded perspective view of the x-ray device enclosure unit of FIG. 13A.
Figure 15:
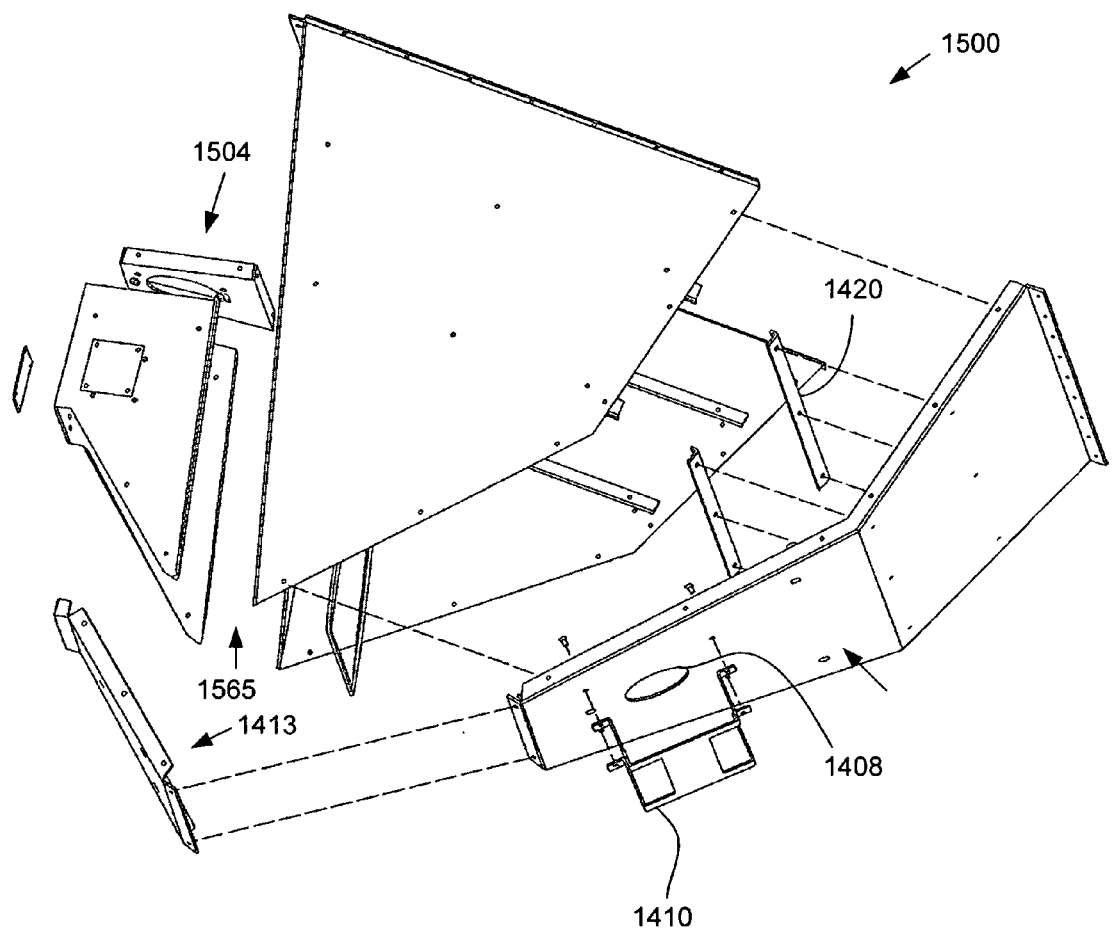
FIG. 15 is another exploded perspective view of the X-ray device enclosure unit of FIG. 13A.

FIG. 14 is an exploded perspective view 1400 of the x-ray device enclosure unit of FIG. 13A. A screen, such as that shown at 110 in FIG. 100 can be mounted within the mirror box 1301 on flanges 1418, 1420 which protrude into the center of the box such that substantially all light is blocked. Mounts 1406, 1412 and 1414, which can be kinematic mounts, can be preferably used to mount a camera or other light measuring device, such as that shown at 408 (FIG. 4) to be focused with minimal parallax and keystoning. In an exemplary embodiment, 27 different angles can be adjusted on the mirror box to facilitate camera focus.

A mirror, such as the mirror 406 (FIG. 4) which can be used to bend the light path to allow the camera mounted outside the mirror box to capture substantially all of the x-ray image, can be mounted on all or a portion of the surfaces shown at 1422. This mirror may be used to at least partially produce a folded light path, such that the light image traveling along the folded light path is reflected by the mirror, a first segment of the light image crossing a second segment of the light image at least twice, the mirror substantially focusing the light image on a camera, such as the light-sensing device at 408 (FIG. 4). An exemplary embodiment of the folded light path is shown at 310 and 315 (FIG. 3).

Figure 16A:
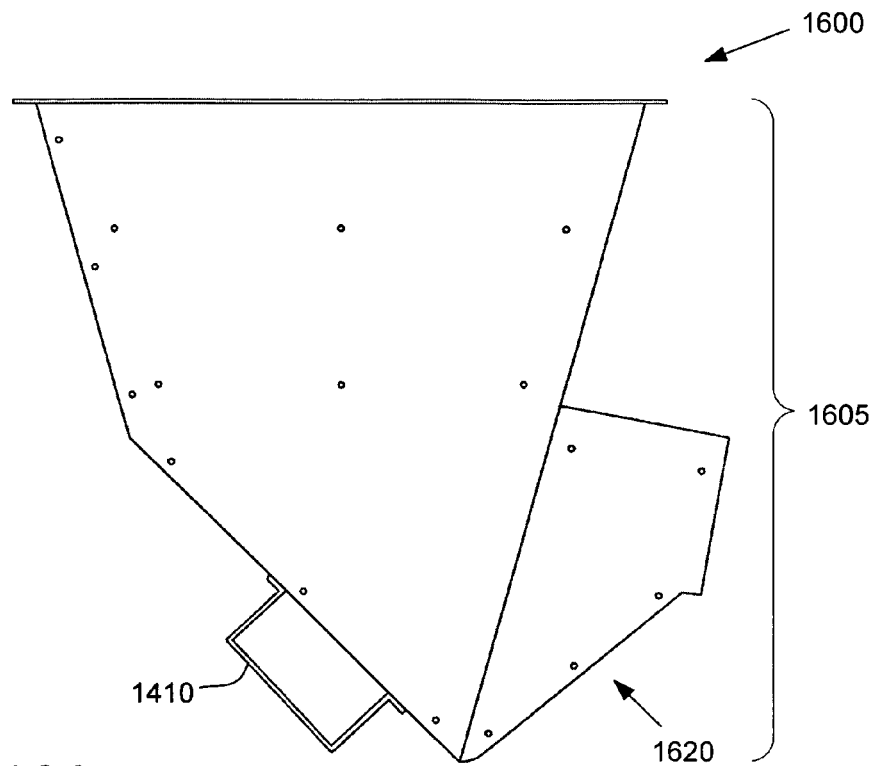
FIG. 16A is an elevation view of another embodiment of an X-ray device enclosure unit.
Figure 16B:
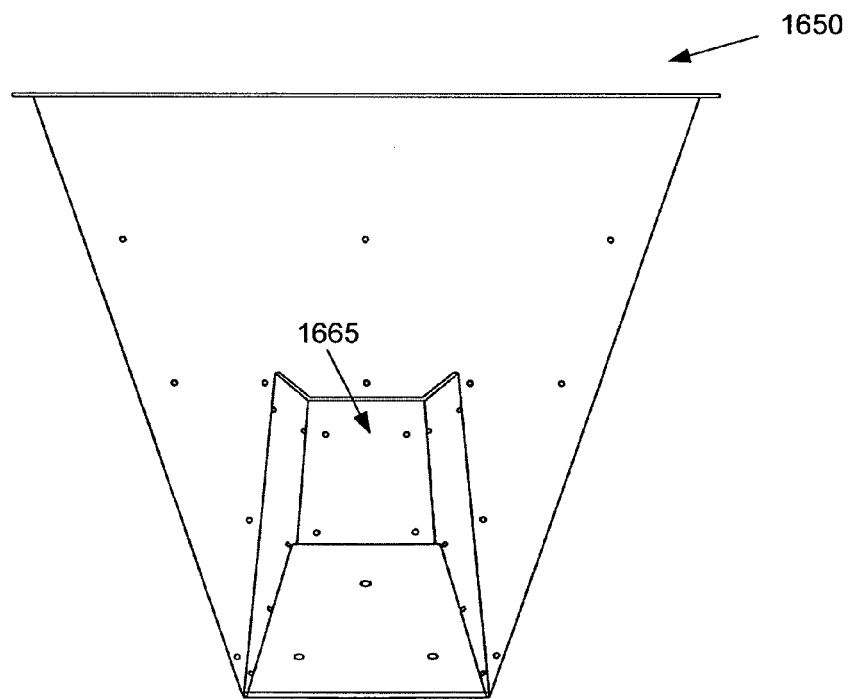
FIG. 16B is a cutaway view of the X-ray device enclosure unit of FIG. 16A.
Figure 16C:
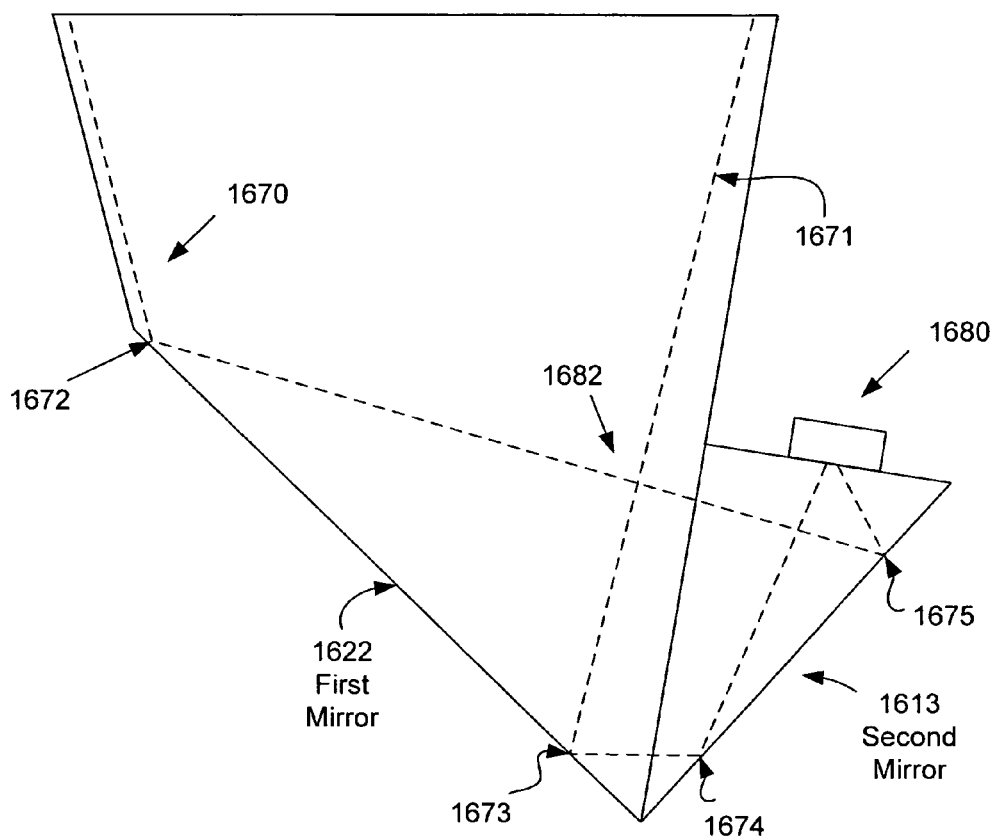
FIG. 16C is a cutaway view of the elevation of FIG. 16A showing an exemplary light path.

Another exemplary embodiment of the folded light path is shown at 1670 and 1671 of FIG. 16C.

A camera box 1415 (such as the camera box 1306 in FIG. 3) is mounted flush with the mirror box 1350 with an aperture (embodiments shown at 1365, 1565 and 1665) between them. A mirror 1422 can be mounted at substantially a 45 degree angle to this aperture, though other angles of mounting are envisioned. Additionally, the mirror 1422 may be enhanced by surface preparation to provide additional light reflection when mounted approximately between 78 degrees and 120 degrees to the incident light beam. The mirror 1422 may reflect in excess of 97.5% of the available light, and may be aluminum-enhanced, and micro- or pico-ground.

The camera box 1415 has a second mirror mounted on the surface shown at 1613 (FIG. 16). This mirror surface 1613, also shown at 1413 (FIGS. 14 and 15.) can be mounted at an angle substantially 85 degrees incident to the mirror box mirror 1422. Additionally, the mirror 1613 may be enhanced by surface preparation to provide additional light reflection when mounted approximately between 45 degrees and 112 degrees to the incident light beam. The mirror 1613 may reflect in excess of 97.5% of the available light, and may be aluminum-enhanced, and micro- or pico-ground.

Brackets 1418, 1420 can be used to ensure that a screen, such as the screen 110 is impervious to light, and that it is mounted securely.

A photon detection device, such as that shown at 414 (FIG. 4), such as an ionization chamber, may be mounted substantially outside of the mirror box; such as in the brackets shown at 1410.

An opening is shown at 1408 between the photon detection device and the mirror box. In an exemplary embodiment, the mirror 406 (FIG. 4) is permeable to X-rays; and covers the opening 1408 between the photon detection device 414 (FIG. 4) and the mirror box 1301 (FIG. 13). The photon detection device 414 (FIG. 4) can be mounted, such as with the brackets 1410, such that at least a portion of an X-ray image (X-rays 105 or light photons 110) strikes the photon detection device 414 (FIG. 4) through the mirror 406 (FIG. 4).

FIG. 15 is an exploded perspective view 1500 of the X-ray device enclosure unit of FIG. 13A shown from the opposite side of the device than that shown in FIG. 14. A bracket 1504 on camera box 1582 is shown which can be used to mount a light measuring device, such as the light measuring device 408.

X. EXEMPLARY SYSTEM EMBODIMENT SHOWING MIRROR PLACEMENT AND LIGHT PATH

FIG. 16A is an elevation view 1600 of another embodiment of an X-ray device enclosure unit similar to FIG. 13A. Mounting brackets 1410 which can be used to hold a photon detection device are shown. In an exemplary embodiment, the height of the mirror box 1600 is 16.11 inches. The camera box (embodiments also shown at 1306, 1415 and 1565) is shown at 1615. FIG. 16B is elevation cutaway view 1650 of the X-ray device enclosure unit of FIG. 16A.

FIG. 16C shows an exemplary embodiment of a folded light path used, for example, to allow a light measuring device (such as the light measuring device 408 of FIG. 4) positioned outside the path of X-rays (such as the X-rays 105 of FIG. 1) to receive an X-ray image.

FIG. 16C has a first mirror 1622, mounted at substantially a 45 degree angle to the aperture 1684 located between a mirror box 1669 and a camera box 1682. A second mirror 1613 is located on the inside diagonal surface of the camera box 1682. A X-ray image enters from the top of the beam enclosure 120 (FIG. 1), and is converted at least partially into light photons 115 (FIG. 1). These light photons 115 (FIG. 1) are reflected by the first mirror 1622 to the second mirror 1613. The degree of the reflection depends upon where along the surface of the mirror the light photon hits, with photons hitting nearer the bottom of the mirror reflecting at a more acute angle, such as the angle 1673 formed by the exemplary light segment 1671, than those hitting nearer the top of the mirror, such as the angle 1672 formed by the exemplary light segment 1670.

When the rays hit the second mirror, they are reflected towards lens of a light-measuring device 1618. Rays that hit lower on the mirror are reflected at a more obtuse angle, such as the angle 1674 of light segment 1671 than those that hit nearer the top of the mirror, such as the angle 1675 of light segment 1670.

It can be seen that each light ray crosses the path of at least one other light ray at least twice. The two exemplary light segments in the example cross, for example, at 1686 and 1688.

XI. Computing Environment

Figure 17:
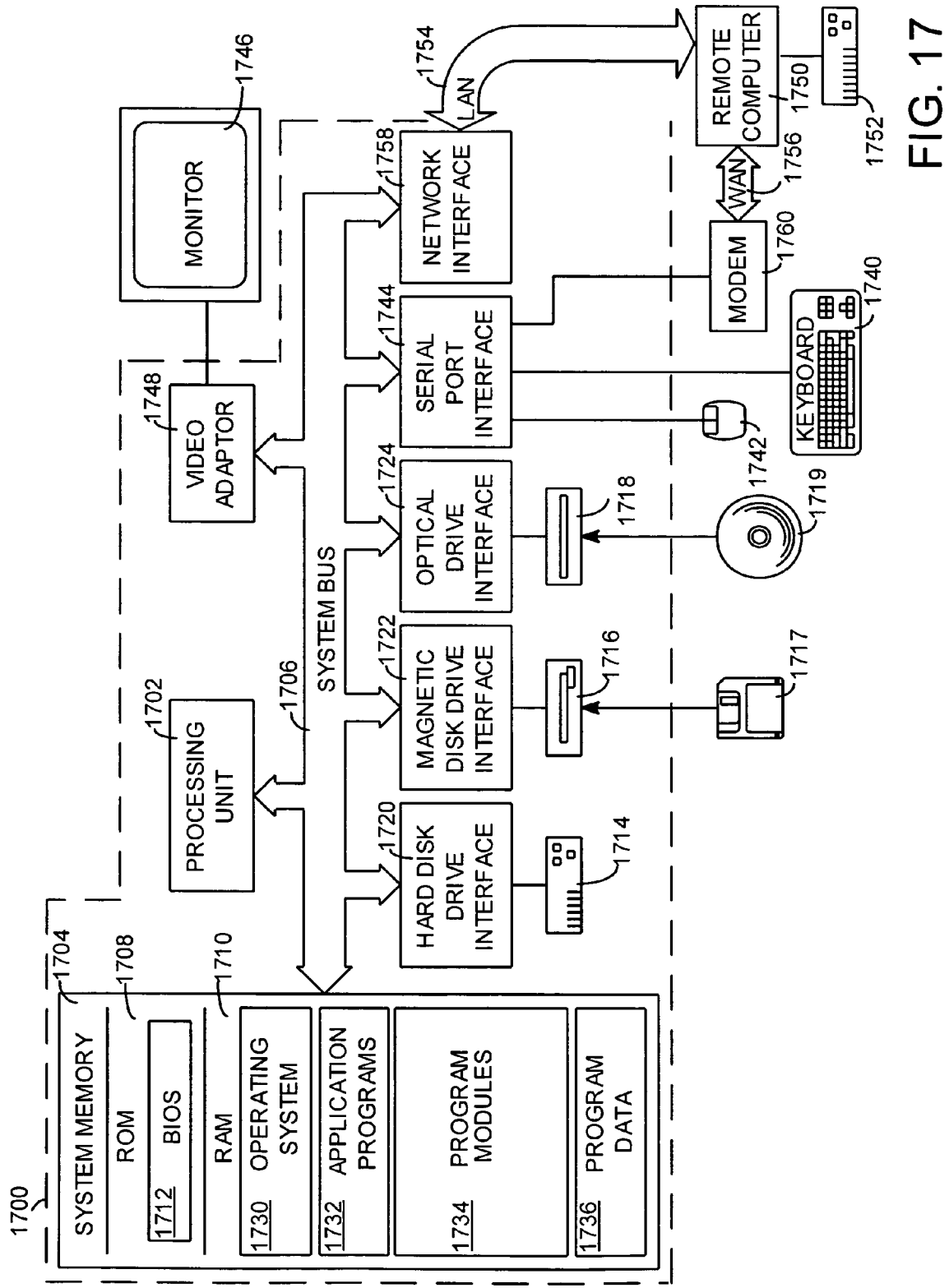
FIG. 17 is a block diagram of a suitable computing environment in conjunction with which described exemplary embodiments may be implemented.

With reference to FIG. 17, an exemplary system for implementing at least portions of the disclosed technology includes a general purpose computing device in the form of a conventional computer 1700, which may be a PC, or a larger system, including a processing unit 1702, a system memory 1704, and a system bus 1706 that couples various system components including the system memory 1704 to the processing unit 1702. The system bus 1706 may be any of several types of bus structures, including a memory bus or memory controller, a peripheral bus, and a local bus using any of a variety of bus architectures. The system memory 1704 includes read only memory (ROM) 1708 and random access memory (RAM) 1710. A basic input/output system (BIOS) 1712, containing the basic routines that help with the transfer of information between elements within the computer 1700, is stored in ROM 1708.

The computer 1700 further includes one or more of a hard disk drive 1714 for reading from and writing to a hard disk (not shown), a magnetic disk drive 1716 for reading from or writing to a removable magnetic disk 1717, and an optical disk drive 1718 for reading from or writing to a removable optical disk 1719 (such as a CD-ROM or other optical media). Flash memory (not shown) may also be used to store information. These disks 1714, 1716, 1717, 1718, and 1719, the hard drive and the flash memory may be used separately or in combination to store digital X-ray images. Furthermore a cataloging system may also be included to allow easy retrieval of a desired image.

The hard disk drive 1714, magnetic disk drive 1716, and optical disk drive 1718 (if included) are connected to the system bus 1706 by a hard disk drive interface 1720, a magnetic disk drive interface 1722, and an optical drive interface 1724, respectively. The drives and their associated computer-readable media provide nonvolatile storage of computer-readable instructions, data structures, program modules, and other data for the computer 1700. They may also be used to store algorithms used to process, store, and retrieve the digital images, as well as other algorithms used in conjunction with the digital X-ray images. Other types of computer-readable media which can store data that is accessible by a computer, such as magnetic cassettes, flash memory cards, digital video disks, CDs, DVDs, RAMs, ROMs, and the like (none of which are shown), may, also be used in the exemplary operating environment.

A number of program modules may be stored on the hard disk 1714, magnetic disk 1717, optical disk 1719, ROM 1708, or RAM 1710, including an operating system 1730, one or more application programs 1732, including applications to manipulate, store, transfer, etc. the digital X-ray images, other program modules 1734, and program data 1736. A user may enter commands and information into the computer 1700 through input devices, such as a keyboard 1740 and pointing device 1742 (such as a mouse). Other input devices (not shown) may include a digital camera, microphone, joystick, game pad, satellite dish, scanner, or the like (also not shown). These and other input devices are often connected to the processing unit 1702 through a serial port interface 1744 that is coupled to the system bus 1706, but may be connected by other interfaces, such as a parallel port, game port, or universal serial bus (USB) (none of which are shown). A monitor 1746 or other type of display device is also connected to the system bus 1706 via an interface, such as a video adapter 1748. This monitor 1746 may be used to display the digital X-ray images. Other peripheral output devices, such as speakers and printers (not shown), may be included.

The computer 1700 may operate in a networked environment using logical connections to one or more remote computers 1750, and to a remote-triggered X-ray imaging system as shown, for example, in FIG. 1. The remote computer 1750 may be another computer, a server, a router, a network PC, or a peer device or other common network node, and typically includes many or all of the elements described above relative to the computer 1700, although only a memory storage device 1752 has been illustrated in FIG. 17. The logical connections depicted in FIG. 17 include a local area network (LAN) 1754 and a wide area network (WAN) 1756. Such networking environments are commonplace in offices, enterprise-wide computer networks, intranets, and the Internet.

When used in a LAN networking environment, the computer 1700 is connected to the LAN 1754 through a network interface 1758. When used in a WAN networking environment, the computer 1700 typically includes a modem 1760 or other means for establishing communications over the WAN 1756, such as the Internet. The connection may be a wireless connection. The modem 1760, which may be internal or external, is connected to the system bus 1706 via the serial port interface 1744. In a networked environment, program modules depicted relative to the computer 1700, or portions thereof, may be stored in the remote memory storage device 1752. Digital X-ray images may also be stored in the remote memory storage device 1752. The network connections shown are exemplary, and other means of establishing a communications link between the computers may be used.

XII. Alternatives

Having described and illustrated the principles of our various embodiments with reference to the illustrated embodiments, it will be recognized that the illustrated embodiments can be modified in arrangement and detail without departing from such principles.

Examples of object sizes, relative ratios between parts, angles shown, etc. are examples only and can be modified appropriately. Also, the technologies from any example can be combined with the technologies described in any one or more of the other examples.

In view of the many possible embodiments, it should be recognized that the illustrated embodiments are examples only and should not be taken as a limitation on scope. For instance, various components of systems and methods described herein may be combined in function and use. We therefore claim as our invention all subject matter that comes within the scope and spirit of these claims.

I claim:

1. A system comprising:
    an X-ray to light converter which converts an x-ray image to a light image;
    a mirror box with a camera opening;
    a first mirror mounted within the mirror box;
    a second mirror mounted within the mirror box;
    a light measuring device mounted substantially outside of the mirror box behind the camera opening;
    an ionization chamber mounted substantially outside of the mirror box; there being an opening between the ionization chamber and the mirror box; the ionization chamber operationally able to trigger the light measuring device in the presence of x-rays;
    wherein the first and second mirrors are arranged such that a folded light path is created such that a first segment of the light image crosses a second segment of the light image, the mirrors substantially transmitting the light image to the light measuring device.

2. The system of claim 1 wherein the mirror box dissipates sufficient heat that no other heat-dissipation device is used for the light measuring device.

3. The system of claim 1 wherein the first mirror is permeable to x-rays; wherein the first mirror covers the opening between the ionization chamber and the mirror box; and wherein the ionization chamber is mounted such that at least a portion of the x-ray image strikes the ionization chamber through the mirror.

4. The system of claim 1 wherein the light measuring device is mounted on a camera box and wherein the camera box comprises at least ten points of adjustment such that the angle of the camera can be adjusted such that substantially all of at least one of parallax and keystoning can be removed.

5. The system of claim 1 wherein the first and second mirrors are arranged such that the first segment of the light image crosses the second segment of the light image at least twice.

6. The system of claim 1 wherein the light measuring device is connected to a computer by a network, the network operationally able to transfer a digital representation of the light image to the computer.

7. The system of claim 6 further comprising imaging software, the imaging software operationally able to display the digital representation of the light image on a display.

8. The system of claim 7 wherein the imaging software is further operationally able to filter the digital representation of the light image based on at least one of species, view, body part, and X-ray energy setting.

9. The system of claim 7 wherein the first mirror is mounted at an angle of substantially 45 degrees from the camera opening.

10. The system of claim 9 wherein the second mirror is mounted substantially at an 85 degree angle from the first mirror.

11. The system of claim 10 wherein the camera is mounted substantially at a 50 degree angle from the second mirror.

12. A system comprising:
    an x-ray to light converter which converts an x-ray image to a light image;
    a mirror box with a camera opening and an ionization chamber opening;
    a mirror mounted within the mirror box over the ionization chamber opening;
    a camera mounted substantially outside of the mirror box above the camera opening; and
    an ionization chamber mounted substantially outside the mirror box behind the ionization chamber opening; the ionization chamber operationally able to trigger the camera in the presence of x-rays; wherein the mirror is permeable to x-rays; and wherein the ionization chamber is mounted such that at least a portion of the x-ray image strikes the ionization chamber.

13. The system of claim 12 further comprising a folded light path, such that the light image traveling along the folded light path is reflected by the mirror, a first segment of the light image crossing a second segment of the light image at least twice, the mirror substantially transmitting the light to the camera.

14. The system of claim 13 further comprising a second mirror, the second mirror mounted such that at least a portion of the folded light path strikes the second mirror.

15. The system of claim 12 wherein the mirror box has a height of at most 17 inches.

16. The system of claim 12 wherein the mirror box has a width of at most 18.5 inches.

17. A method of generating an X-ray image, comprising:

converting at least some X-ray photons generated from an X-ray source to light photons;

using an ionization chamber to trigger charge-coupled device camera when the ionization chamber detects photons in an amount greater than a threshold amount, the charge-coupled device camera being out of the path of the X-ray photons; and using a first mirror to reflect light path of the light photons such that substantially all of the light photons are reflected towards a second mirror, the second mirror reflecting substantially all of the light photons toward the charge-coupled device camera; thereby generating an X-ray image.

18. The method of claim 17 wherein the first mirror bends the light photons at angles between 120 degrees and 78 degrees.

19. The method of claim 17 wherein the second mirror bends the light photons at angles between 45 and 112 degrees.

* * * * *